United States Patent
Eichler et al.

(10) Patent No.: US 12,276,670 B2
(45) Date of Patent: Apr. 15, 2025

(54) METHODS FOR IDENTIFYING AND TREATING ADRENOMYELONEUROPATHY (AMN)

(71) Applicant: The General Hospital Corporation, Boston, MA (US)

(72) Inventors: Florian Eichler, Cambridge, MA (US); Yi Gong, Malden, MA (US)

(73) Assignee: The General Hospital Corporation, Boston, MA (US)

( * ) Notice: Subject to any disclaimer, the term of this patent is extended or adjusted under 35 U.S.C. 154(b) by 1133 days.

(21) Appl. No.: 16/651,926

(22) PCT Filed: Oct. 1, 2018

(86) PCT No.: PCT/US2018/053709
§ 371 (c)(1),
(2) Date: Mar. 27, 2020

(87) PCT Pub. No.: WO2019/068072
PCT Pub. Date: Apr. 4, 2019

(65) Prior Publication Data
US 2020/0309788 A1    Oct. 1, 2020

Related U.S. Application Data

(60) Provisional application No. 62/565,753, filed on Sep. 29, 2017.

(51) Int. Cl.
*G01N 33/68* (2006.01)
*C07K 16/04* (2006.01)

(52) U.S. Cl.
CPC ......... *G01N 33/6896* (2013.01); *C07K 16/04* (2013.01); *G01N 33/6893* (2013.01); *G01N 2800/52* (2013.01)

(58) Field of Classification Search
CPC ....................... G01N 33/6893; G01N 2800/52
See application file for complete search history.

(56) References Cited

U.S. PATENT DOCUMENTS

| | | |
|---|---|---|
| 5,719,060 A | 2/1998 | Hutchens et al. |
| 2013/0210666 A1* | 8/2013 | Jarvi .................... G01N 33/689 506/18 |
| 2013/0302838 A1 | 11/2013 | Kokai et al. |
| 2017/0138963 A1 | 5/2017 | Jarvi et al. |
| 2018/0193270 A1 | 7/2018 | Bolen et al. |

FOREIGN PATENT DOCUMENTS

| | | |
|---|---|---|
| WO | WO 98/59361 | 12/1998 |
| WO | WO 2017/009437 | 1/2017 |

OTHER PUBLICATIONS

Berger et al., "Current and future pharmacological treatment strategies in X-Linked adrenoleukodystrophy," Brain Pathol., Jul. 2010, 20(4):845-856.
Berger et al., "Pathophysiology of X-linked adrenoleukodystrophy," Biochimie, Mar. 2014, 98:135-142.
Brown and Neher, "Microglial phagocytosis of live neurons," Nature Reviews Neuroscience, 15(4)209-216.
Brown and Vilalta, "How microglia kill neurons," Brain Research, Dec. 2015, 1628:288-297.
Butovsky et al., "Modulating inflammatory monocytes with a unique microRNA gene signature ameliorates murine ALS," The Journal of Clinical Investigation, Sep. 2012, 122(9):3063-3087.
Dumser et al., "Lack of adrenoleukodystrophy protein enhances oligodendrocyte disturbance and microglia activation in mice with combined Abcd1/Mag deficiency," Acta Neuropathologica, Dec. 2007, 114(6):573-586.
Eichler et al., "Is microglial apoptosis an early pathogenic change in cerebral X-linked adrenoleukodystrophy?," Annals of Neurology, Jun. 2008, 63(6):729-742.
Engelen et al., "X-linked adrenoleukodystrophy (X-ALD): clinical presentation and guidelines for diagnosis, follow-up and management," Orphanet J. Rare. Dis., Dec. 2012, 7(1):51.
Fricker et al., "MFG-E8 mediates primary phagocytosis of viable neurons during neuroinflammation," The Journal of Neuroscience: The Official Journal of the Society for Neuroscience, Feb. 2012, 32(8):2657-2666.
Geel et al., "Hematopoietic cell transplantation does not prevent myelopathy in X-linked adrenoleukodystrophy: a retrospective study," Journal of Inherited Metabolic Disease, Mar. 2015, 38(2):359-361.
Geel et al., "Peripheral nerve abnormalities in adrenomyeloneuropathy: a clinical and electrodiagnostic study," Neurology, Jan. 1996, 46(1):112-118.
Gong et al., Microglial Dysfunction as a Key Pathological Change in Adrenomyeloneuropathy, Annals of Neurology, Oct. 2017, 82(5):813-827.
Gong et al., "Adenoassociated virus serotype 9-mediated gene therapy for x-linked adrenoleukodystrophy," Molecular Therapy : The Journal of the American Society of Gene Therapy, May 2015, 23(5):824-834.
Hein et al., "Toxic effects of X-linked adrenoleukodystrophy-associated, very long chain fatty acids on glial cells and neurons from rat hippocampus in culture," Human Molecular Genetics, Jun. 2008, 17(12):1750-1761.
Hitomi et al., "Long-term effect of bone marrow transplantation in adult-onset adrenoleukodystrophy," Eur. J. Neurol., Oct. 2005, 12(10):807-810.
Ho et al., "Interactions of a very long chain fatty acid with model membranes and serum albumin. Implications for the pathogenesis of adrenoleukodystrophy," The Journal of Clinical Investigation, 96(3):1455-1463.

(Continued)

*Primary Examiner* — Olga N Chernyshev
(74) *Attorney, Agent, or Firm* — Fish & Richardson P.C.

(57) ABSTRACT

Provided herein is a method of detecting adrenomyeloneuropathy (AMN) in a human male subject, said method comprising determining the level of MFGE8, C1qa, Trem2, Gas6 or any combination thereof, in a biological sample obtained from the spine of the subject, wherein said level or levels are increased compared to a reference level or levels, thereby detecting AMN in the subject. Also provided is a method of treating AMN in a human male subject, said method comprising administering an anti-MFGE8 antibody to the subject.

9 Claims, 25 Drawing Sheets

(56) References Cited

OTHER PUBLICATIONS

Hong et al., "Complement and microglia mediate early synapse loss in Alzheimer mouse models," Science, May 2016, 352(6286):712-716.
Hubbard et al., "Newborn screening for X-linked adrenoleukodystrophy (X-ALD): validation of a combined liquid chromatography-tandem mass spectrometric (LC-MS/MS) method," Molecular Genetics and Metabolism, Jul. 2009, 97(3):212-220.
Igarashi et al., "Fatty acid abnormality in adrenoleukodystrophy," Journal of Neurochemistry, Apr. 1976, 26(4):851-860.
Kim et al., "A 3D human neural cell culture system for modeling Alzheimer's disease," Nature Protocols, Jul. 2015, 10(7):985-1006.
Kinsner et al., "Inflammatory neurodegeneration induced by lipoteichoic acid from *Staphylococcus aureus* is mediated by glia activation, nitrosative and oxidative stress, and caspase activation," Journal of Neurochemistry, Nov. 2005, 95(4):1132-1143.
Köhler et al., "Hematopoietic stem cell transplantation for adult cerebral X-linked adrenoleukodystrophy," Neurology, 2014, 82(10 Supplement):P5.174.
Lui et al., "Progranulin Deficiency Promotes Circuit-Specific Synaptic Pruning by Microglia via Complement Activation," Cell, May 2016, 165(4):921-935.
Mahmood et al., "Survival analysis of haematopoietic cell transplantation for childhood cerebral X-linked adrenoleukodystrophy: a comparison study," The Lancet Neurology, Aug. 2007, 6(8):687-692.
Moser et al., "Plasma very long chain fatty acids in 3,000 peroxisome disease patients and 29,000 controls," Annals of Neurology, Jan. 1999, 45(1):100-110.
Moser, "Adrenoleukodystrophy: phenotype, genetics, pathogenesis and therapy," Brain, Aug. 1997, 120(8):1485-1508.
Moser, "Clinical and therapeutic aspects of adrenoleukodystrophy and adrenomyeloneuropathy," J. Neuropathol. Exp. Neurol., Sep. 1995, 54(5):740-745.
Mosser et al., "Putative X-linked adrenoleukodystrophy gene shares unexpected homology with ABC transporters," Nature, Feb. 1993, 361(6414):726-730.
Mosser et al., "The gene responsible for adrenoleukodystrophy encodes a peroxisomal membrane protein," Human Molecular Genetics, Feb. 1994, 3(2):265-271.
Neher et al., "Inhibition of microglial phagocytosis is sufficient to prevent inflammatory neuronal death," Journal of Immunology, Apr. 2011, 186(8):4973-4983.
Neher et al., "Phagocytosis executes delayed neuronal death after focal brain ischemia," Proceedings of the National Academy of Sciences of the United States of America, Oct. 2013, 110(43): E4098-4107.
Neniskyte & Brown, "Lactadherin/MFG-E8 is essential for microglia-mediated neuronal loss and phagoptosis induced by amyloid beta," Journal of Neurochemistry, Aug. 2013, 126(3):312-317.
Patel & Gutowski, "The difficulty in diagnosing X linked adrenoleucodystrophy and the importance of identifying cerebral involvement," BMJ Case Rep., May 2015, bcr2015209732, 4 pages.
PCT International Preliminary Report on Patentability in International Appln. No. PCT/US2018/053709, dated, Mar. 31, 2020, 7 pages.
PCT International Search Report and Written Opinion in International Appln. No. PCT/US2018/053709, dated Dec. 7, 2018, 10 pages.
Powers et al., "Adrenomyeloneuropathy: a neuropathologic review featuring its noninflammatory myelopathy," Journal of Neuropathology and Experimental Neurology, Feb. 2000, 59(2):89-102.
Powers, "Adreno-leukodystrophy (adreno-testiculo-leukomyelo-neuropathic-complex)," Clinical Neuropathology, Sep. 1985, 4(5):181-199.
Pujol et al., "Functional overlap between ABCD1 (ALD) and ABCD2 (ALDR) transporters: a therapeutic target for X-adrenoleukodystrophy," Human Molecular Genetics, Dec. 2004, 13(23):2997-3006.
Pujol et al., "Late onset neurological phenotype of the X-ALD gene inactivation in mice: a mouse model for adrenomyeloneuropathy," Human Molecular Genetics, Mar. 2002, 11(5):499-505.
Ran et al., "Double nicking by RNA-guided CRISPR Cas9 for enhanced genome editing specificity," Cell, Sep. 2013, 154(6):1380-1389.
Ran et al., "Genome engineering using the CRISPR-Cas9 system," Nature Protocols, Nov. 2013, 8(11):2281-2308.
Ransohoff & Khoury, "Microglia in Health and Disease," Cold Spring Harbor perspectives in biology, Jan. 2016, 8(1):a020560, 16 pages.
Schafer et al., "Microglia sculpt postnatal neural circuits in an activity and complement-dependent manner," Neuron, May 2012, 74(4):691-705.
Schaumburg et al., "Adrenomyeloneuropathy: a probable variant of adrenoleukodystrophy. II. General pathologic, neuropathologic, and biochemical aspects," Neurology, Dec. 1977, 27(12):1114-1119.
Stephan et al., "A dramatic increase of C1q protein in the CNS during normal aging," The Journal of Neuroscience : the Official Journal of the Society for Neuroscience, 33(33):13460-13474.
Suzuki et al., "Calcium-dependent phospholipid scramblase activity of TMEM16 protein family members," The Journal of Biological Chemistry, May 2013, 288(19):13305-13316.
Suzuki et al., "Xk-related protein 8 and CED-8 promote phosphatidylserine exposure in apoptotic cells," Science, Jul. 2013, 341(6144):403-406.
Tamashiro et al., "Primary microglia isolation from mixed glial cell cultures of neonatal rat brain tissue," JoVE (Journal of Visualized Experiments), 15(66):e3814.
Tyurina et al., "Nitrosative stress inhibits the aminophospholipid translocase resulting in phosphatidylserine externalization and macrophage engulfment: implications for the resolution of inflammation," The Journal of Biological Chemistry, 282(11):8498-8509.
Walport, "Complement," N. Engl. J. Med., Apr. 2001, 344(14):1058-1066.
Whitcomb et al., "Effects of long-chain, saturated fatty acids on membrane microviscosity and adrenocorticotropin responsiveness of human adrenocortical cells in vitro," The Journal of Clinical Investigation, Jan. 1988, 81(1):185-188.

* cited by examiner

METHODS FOR IDENTIFYING AND TREATING ADRENOMYELONEUROPATHY (AMN)

CLAIM OF PRIORITY

This application is a § 371 National Stage Application of PCT/US2018/053709, filed Oct. 1, 2018, which claims the benefit of U.S. Provisional Application Ser. No. 62/565,753, filed on Sep. 29, 2017. The entire contents of the foregoing are incorporated herein by reference.

TECHNICAL FIELD

Described herein are methods for diagnosing and treating adrenoleukodystrophy.

BACKGROUND OF THE INVENTION

X-linked adrenoleukodystrophy (X-ALD) is caused by mutations in ABCD1, a gene that encodes the peroxisomal half-transporter adenosine triphosphate-binding cassette domain I (ABCD1) (Mosser et al., 1993; Mosser et al., 1994). The most severe form of X-ALD, childhood cerebral ALD (CALD), manifests as acute demyelination in childhood with prominent lymphocytic infiltration and a distinct zone of microglial cell death surrounding the inflammatory lesion (Berger et al., 2014; Eichler et al., 2008). The more common phenotype is adrenomyeloneuropathy (AMN), an axonopathy of the spinal cord with notable absence of inflammatory lesions or lymphocytic infiltration but numerous microglia and macrophages. There is no genotype-phenotype correlation and the two distinct neurological phenotypes frequently exist within the same family. All male patients who survive into adulthood manifest some degree of axonopathy, making AMN the default manifestation of ABCD1 dysfunction.

Mutations in ABCD1 result in the accumulation of unbranched saturated very long chain fatty acids (VLCFA) in body fluid and tissues (Ho et al., 1995; Igarashi et al., 1976; Moser et al., 1999), and the highest concentrations of VLCFAs reside within lysophosphatidylcholine (LPC) (Hubbard et al., 2009) High-dose LPC injections lead to brain demyelination in mice, but the impact of LPC upon axonal degeneration and AMN pathogenesis has not been studied (Eichler et al., 2008). Notably, levels of VLCFA in plasma do not correlate with phenotype or severity, and attempts at lowering VLCFA have so far shown no effect upon AMN progression.

These discrepancies may be resolved by a closer examination of the cellular constituents of pathology in relation to ABCD1 gene expression. ABCD1 is not uniformly expressed across different cell types. How can axons be affected when ABCD1 is only expressed in neurons at very low levels? Microglia have recently been implicated as potential cellular mediators of synapse loss (Hong et al., 2016). Specific transcriptional and functional alterations of microglia vary in each neurological disease depending on pathology and type of molecular stimuli encountered (Ransohoff and El Khoury, 2015). As ABCD1 is highly expressed in microglia, it is possible that microglial dysfunction is a primary event in AMN and not secondary to neuroinflammation or metabolic abnormalities.

Importantly, ABCD1 deficiency in mice also leads to axonal degeneration, resembling findings in AMN patients (Powers et al., 2000). In AMN mice, previous studies have noted that microglial activation coincides with non-inflammatory axonal degeneration (Dumser et al., 2007; Pujol et al., 2004); similar observations have been made in human AMN spinal cord (Powers et al., 2000). Despite these findings, no detailed studies on the molecular and functional change of microglia in the absence of ABCD1 have been conducted, and the impact of microglia upon long tract degeneration remains unclear.

SUMMARY OF THE INVENTION

It has now been discovered that methods of detecting adrenomyeloneuropathy (AMN) in human male subjects diagnosed with X-linked adrenoleukodystrophy (X-ALD) are possible using newly identified biomarkers.

Thus, provided herein is a method of detecting adrenomyeloneuropathy (AMN) in a human male subject diagnosed with X-linked adrenoleukodystrophy (X-ALD), said method comprising determining the level of MFGE8, C1qa, Trem2, Gas6 or any combination thereof, in a biological sample obtained from the spine of the subject, wherein said level or levels are increased compared to a reference level or levels, thereby detecting AMN in the subject.

In some embodiments, the reference level is a level of any one of MFGE8, C1qa, Trem2, or Gas6 obtained from a human male subject that does not have AMN.

In some embodiments, the method further comprises determining the level of TNF alpha and/or ILI1 beta in the biological sample, wherein said level or levels are decreased compared to a reference level or levels, thereby determining that the patient does not have childhood cerebral ALD (CALD).

In some embodiments, the reference level is a level of TNF alpha and/or ILI1 beta obtained from a human male subject that has been diagnosed with CALD.

In addition, provided herein is a method of selecting a treatment correlated with a good clinical response in a human male subject diagnosed with X-linked adrenoleukodystrophy (X-ALD), said method comprising the steps of: a) determining whether there is an increase in the level of MFGE8, C1qa, Trem2, Gas6 or any combination thereof, in a biological sample obtained from the spine of the subject, wherein said level or levels are increased compared to a reference level or levels, thereby identifying AMN in the subject; and b) selecting a treatment comprising phosphatidylserine exposure, an inhibitor of MFGE8, and/or an inhibitor of the microglial vitronectin receptor to administer to the subject, thereby selecting a treatment correlated with a good clinical response in the subject.

In some embodiments, the method further comprises determining the level of TNF alpha and/or ILI1 beta in the biological sample, wherein said level or levels are decreased compared to a reference level or levels, thereby determining that the patient does not have childhood cerebral ALD.

In some embodiments, the method further comprises determining the level of TNF alpha and/or ILI1 beta in the biological sample, wherein said level or levels further identify childhood cerebral ALD in the subject, and additionally selecting a treatment comprising hematopoetic stem cell therapy to administer to the subject.

Also provided herein is a method of treating adrenomyeloneuropathy (AMN) in a human male subject diagnosed with X-linked adrenoleukodystrophy (X-ALD), said method comprising administering an anti-MFGE8 antibody to the subject in an amount and duration sufficient to improve balance and/or gait or bladder function, thereby treating adrenomyeloneuropathy in the subject.

Other features and advantages of the invention will be apparent from the Detailed Description, and from the claims. Thus, other aspects of the invention are described in the following disclosure and are within the ambit of the invention.

BRIEF DESCRIPTION OF THE DRAWINGS

The following Detailed Description, given by way of example, but not intended to limit the invention to specific embodiments described, may be understood in conjunction with the accompanying figures, incorporated herein by reference.

Figure 7A:
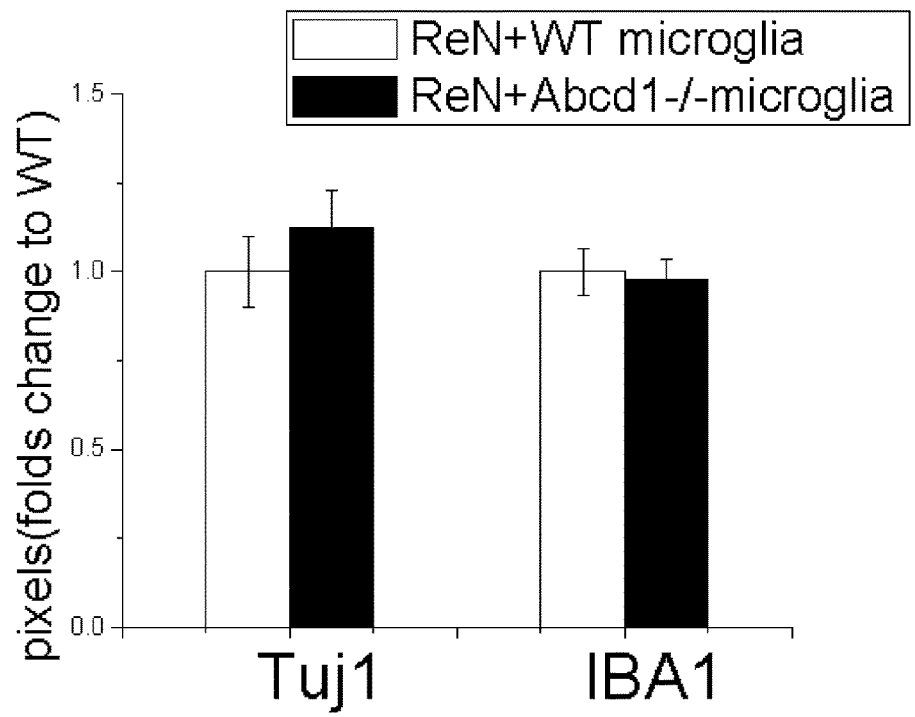
Figure 7B:
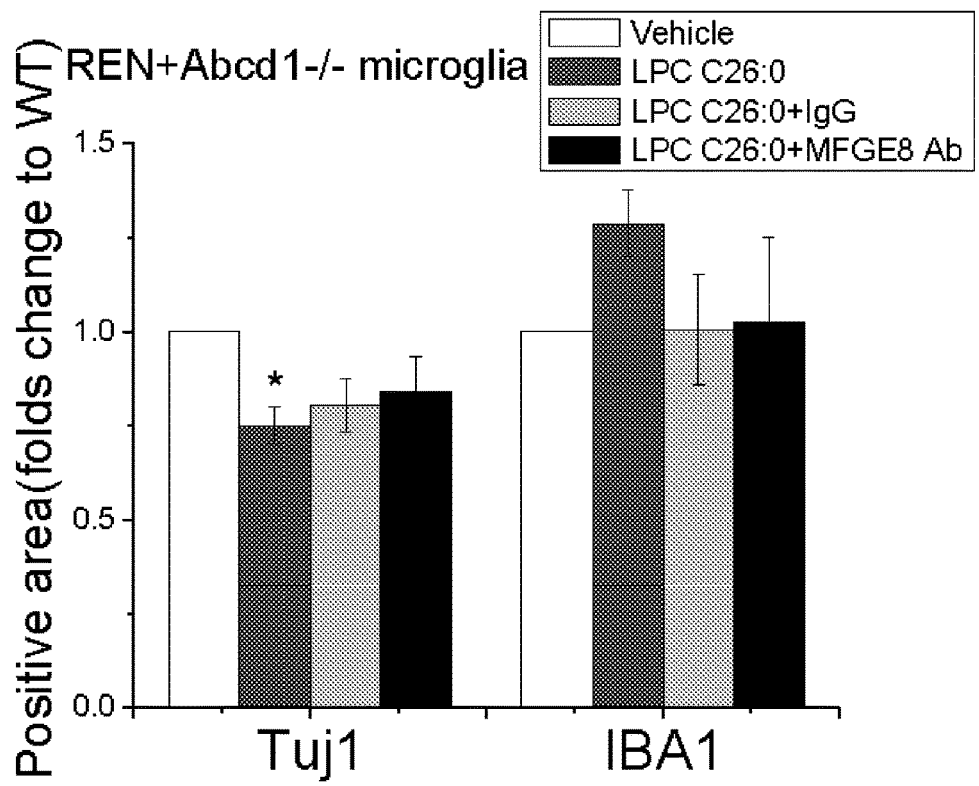
Figure 7C:
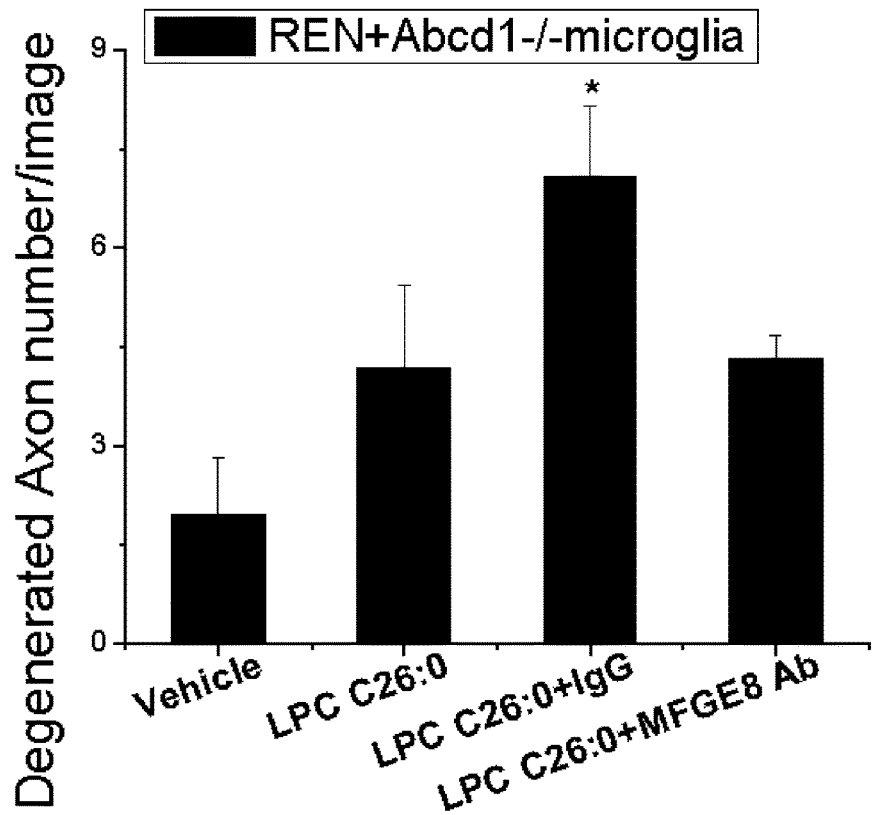
Figure 8A:
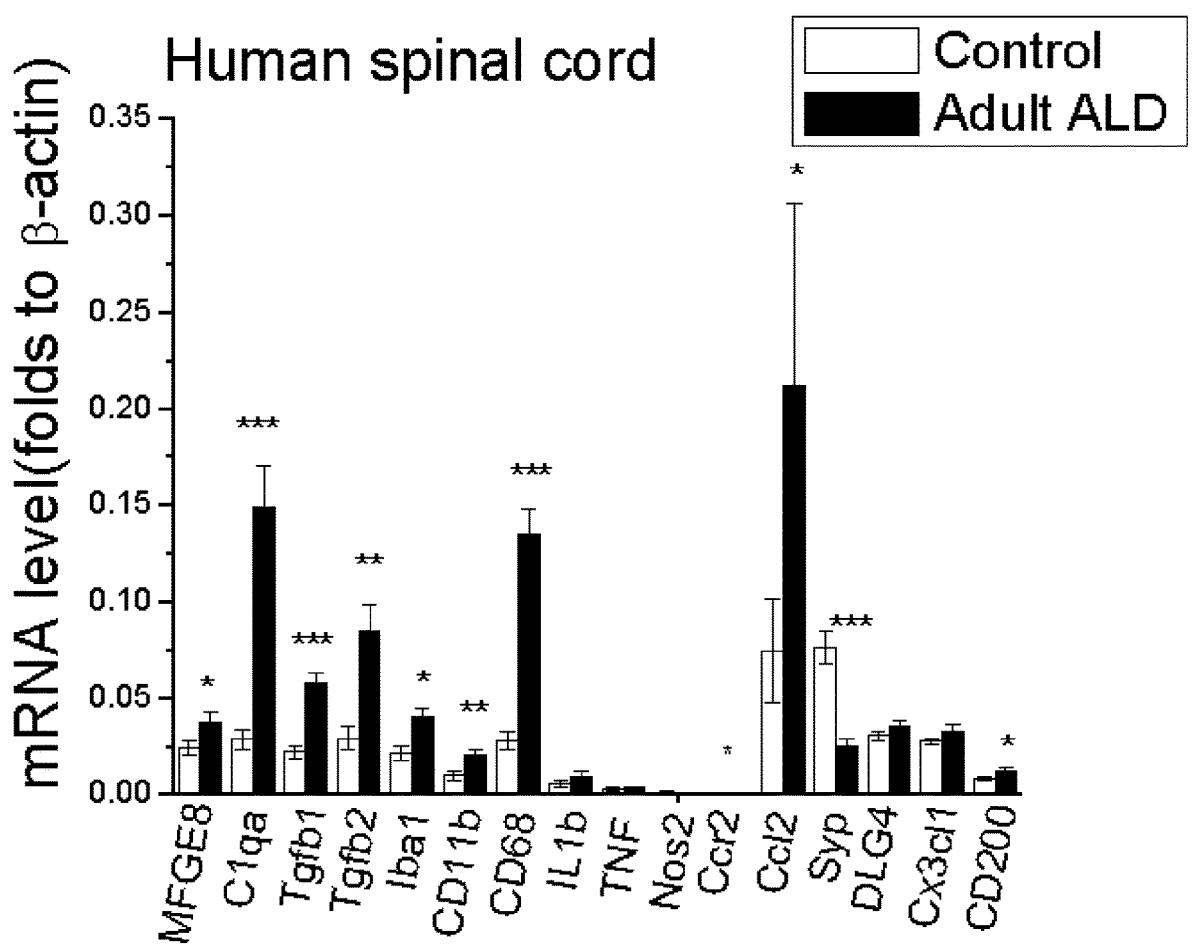
Figure 8B:
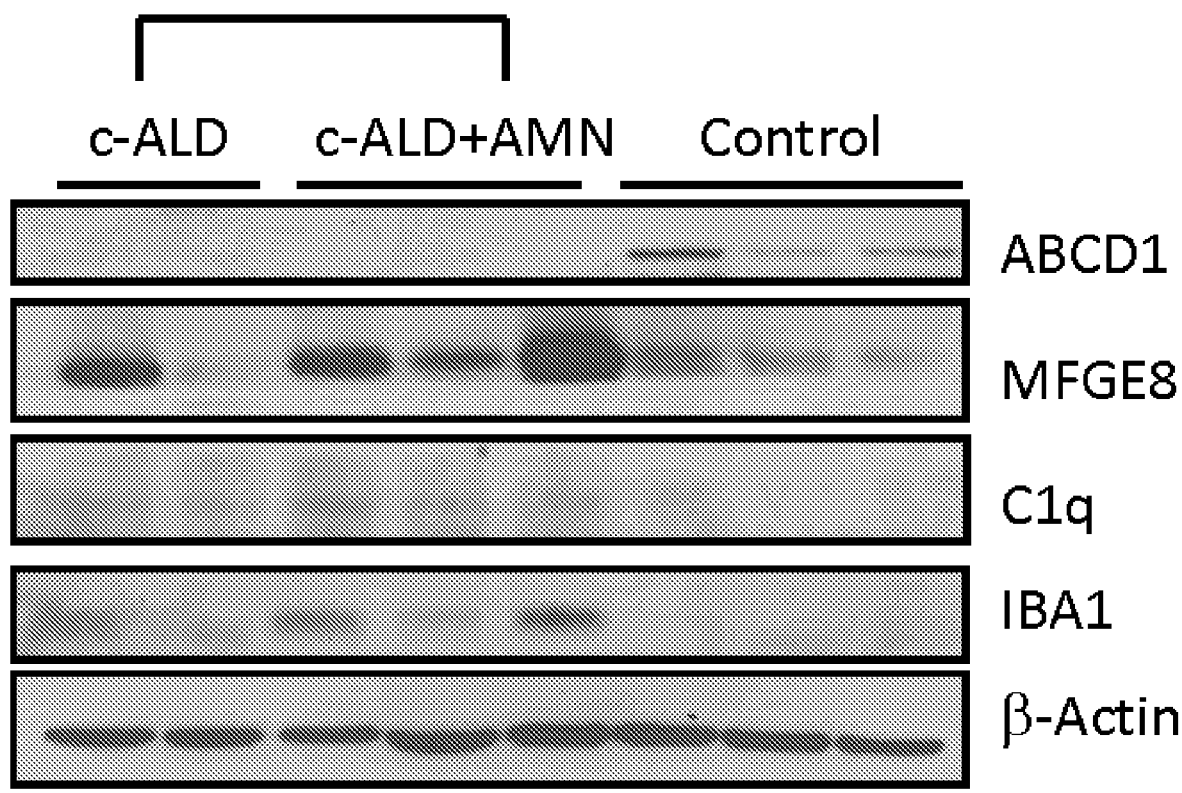
Figure 8C:
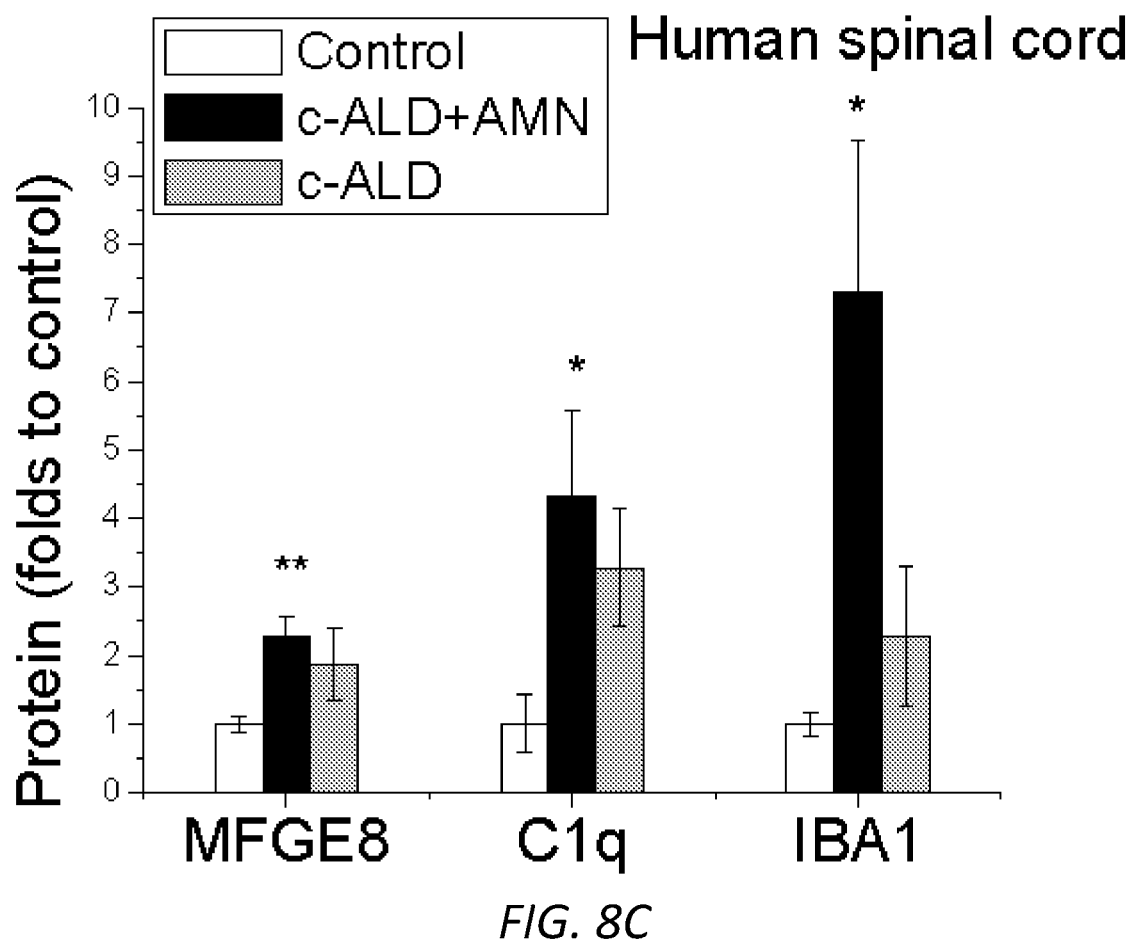
Figure 8D:
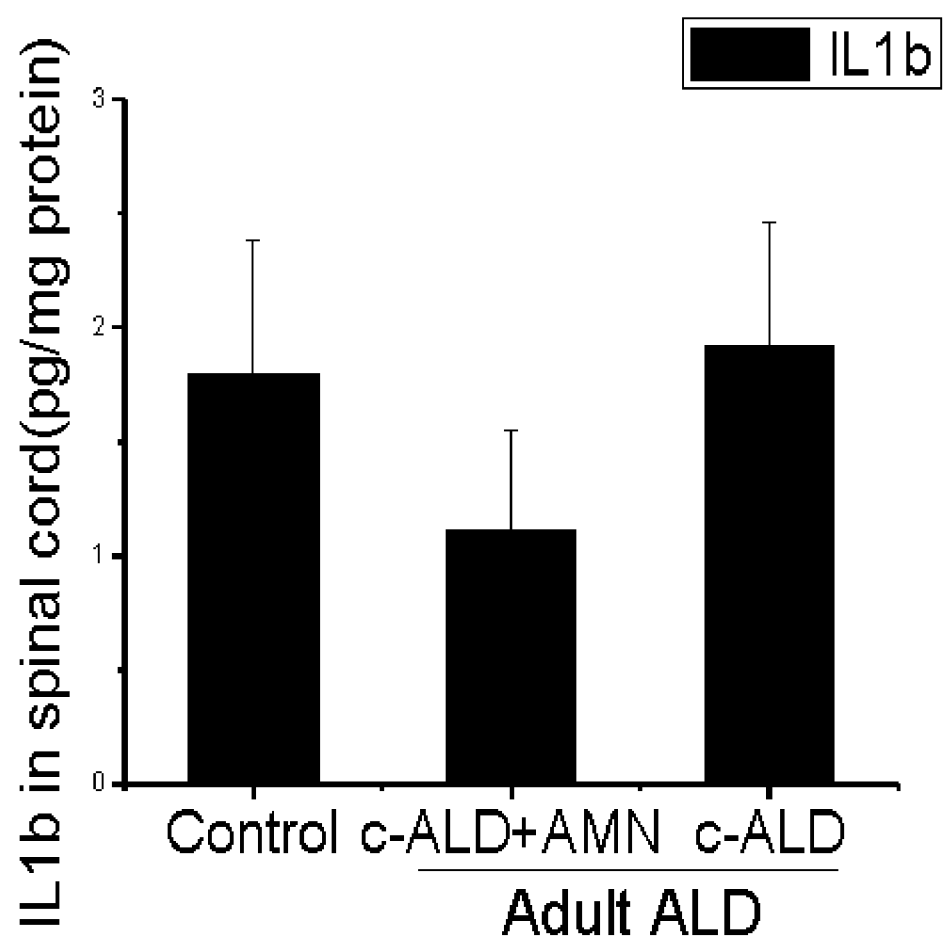

FIGS. 7A-7C depicts LPC C26:0 treatment causing neuronal damage in the co-culture system with Abcd1-/- microglia. Images of co-cultured differentiated neuron with wild type and Abcd1-/- microglia at normal condition were obtained. (A) Image J quantification of Tuj 1 (neurons) and IBA1 (microglia) after co-culture of differentiated neurons and primary microglia for 4 days at regular condition is shown. (B) Effect of 15 uM LPC C26:0 on Tuj 1 expression of differentiated ReN cells in the co-culture system with primary Abcd1-/- microglia and the impact of MFGE8 antibody supplementation is shown. Bar=50 µm. Images of microglia phagocytosing neurons and degenerated axons within co-culture system with LPC C26:0 supplementation were obtained. (C) The graph shows quantification of degenerated axons in the co-culture system. Data were expressed as mean±SEM, *P<0.05.

FIGS. 8A-8D depict microglial activation and phagocytosis in human AMN spinal cord despite unaltered proinflammatory gene expression. LFB staining demonstrated mild myelin loss commensurate with axonal loss. Increased CD68 and IBA1 expression indicated microglia activation in spinal cord. Perivascular macrophages were visible. (A) Gene expression of microglia activation (CD68, phogocytosis (MFGE8, C1qa) and its regulator (TGFb1, TGFb2) as well as monocyte infiltration (CCR2, CCL2) was increased in adult ALD spinal cord, coinciding with evidence of axon degeneration (decrease in SYP), but proinflammatory markers such as TNF and IL1b are unchanged. (B) Representative western blot image shows protein expression of MFGE8, C1q and IBA1 in human ALD spinal cord. (C) Quantification shows increased MFGE8, C1q and IBA1 expression in human ALD spinal cord with β-actin as loading control. (D) Less IL1β expression in AMN compared to cerebral ALD spinal cord. Confocal imaging showed microglial activation in human ALD spinal cord with IBA1 and synaptophysin co-staining. Data were expressed as mean±SEM, *P<0.05, P<0.01, *P<0.001.

DETAILED DESCRIPTION OF THE INVENTION

The data presented herein depicts the role of the innate immune system in the pathogenesis of AMN. As the more acute phenotype of cerebral ALD is associated with microglial activation in the presence of lymphocytic inflammation, it was surprising to find that microglial activation in AMN mouse and human spinal cord not only lacked proinflammatory markers, but was also accompanied by distinct upregulation of phagocytosis; microglial activation precedes axonal degeneration, and that aberrant phagocytosis impairs neuronal projections. Microglial activation is an early change yet no inflammation is seen in spinal cord. Unexpectedly, it was determined that even in young Abcd1-/- mice, several key receptors and signaling molecules for phagocytosis are elevated and therefore function as biomarkers and therapeutic targets in the detection and treatment of AMN. Trem2 gene expression is markedly increased early on, and over time increased expression of milk fat globule EGF factor 8 (MFGE8; also known as lactadherin or SED1) and C1q occur. MFGE8 is known to opsonize dying cells and bind to integrins on the surface of phagocytic cells, thus mediating engulfment.

Recent observations also indicate that microglial engulfment of live neurons plays a significant role in neurodegenerative diseases (Brown and Neher, 2014; Brown and Vilalta, 2015). Both the literature (Fricker et al., 2012; Neher et al., 2013; Neniskyte and Brown, 2013) and the data presented herein confirms that phagocytosis of neurons and axons with exposed phosphatidylserine can be mediated by MFGE8. In general, two requisites are necessary for microglial engulfment of live neurons and axons. The first is activated microglia with upregulated microglial receptors and opsonins like MFGE8, which can recognize a stressed neuron and tag it for engulfment. The second is phosphatidylserine exposure on the neuronal cell surface, which can occur as a result of oxidative stress, an increase in calcium levels, or ATP depletion, among other possible mechanisms (Suzuki et al., 2013a; Suzuki et al., 2013b; Tyurina et al., 2007). Phosphatidylserine exposure is not itself toxic to neurons but rather marks the neuron for selective removal by microglia. If activated microglia are present, this results in phagocytosis of the phosphatidylserine-exposed neurons (Fricker et al., 2012; Neher et al., 2013; Neher et al., 2011; Neniskyte and Brown, 2013). Ultimately, detecting phagocytosis in the spinal cord will be predictive of the AMN phenotype and blocking phagocytosis (hence blocking neurodegeneration) will be therapeutically beneficial in patients with AMN.

Definitions

Unless otherwise defined, all technical and scientific terms used herein have the same meaning as commonly understood by one of ordinary skill in the art to which this invention belongs. In case of conflict, the present application, including definitions will control.

A "subject" is a human male subject diagnosed with X-linked adrenoleukodystrophy (X-ALD) that is at least about 20 years of age.

As used herein, the terms "treat," "treating," "treatment," and the like refer to reducing or ameliorating adrenomyeloneuropathy and/or symptoms associated therewith. It will be appreciated that, although not precluded, treating adrenomyeloneuropathy does not require that the symptoms associated therewith be completely eliminated.

Adrenomyeloneuropathy, or "AMN," refers to an axonopathy of the spinal cord with notable absence of inflammatory lesions or lymphocytic infiltration but numerous microglia and macrophages. AMN occurs in male patients afflicted with X-linked adrenoleukodystrophy (X-ALD), which is caused by mutations in ABCD1, a gene that encodes the peroxisomal half-transporter adenosine triphosphate-binding cassette domain I (ABCD1) (Mosser et al., 1993; Mosser et al., 1994).

Childhood cerebral ALD, or "CALD", manifests as acute demyelination in childhood with prominent lymphocytic infiltration and a distinct zone of microglial cell death surrounding the inflammatory lesion (Berger et al., 2014; Eichler et al., 2008). CALD occurs in male patients afflicted with X-ALD.

By "an effective amount" is meant the amount of a required agent or composition comprising such agent to ameliorate the symptoms of axonopathy adrenomyeloneuropathy (AMN) relative to an untreated reference. The effective amount of composition(s) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is included in the term "effective amount."

As used herein, "a good clinical response" during the course of therapy for AMN refers to stabilization or improvement in motor and sensory symptoms, for example, improvement in balance and gait in the subject.

Unless specifically stated or clear from context, as used herein, the term "about" is understood as within a range of normal tolerance in the art, for example within 2 standard deviations of the mean. "About" is understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 (as well as fractions thereof unless the context clearly dictates otherwise).

As used herein "an increase in expression" refers to an amount of gene expression or protein expression that is at least about 0.05 fold more (for example 0.1, 0.2, 0.3, 0.4, 0.5, 1, 5, 10, 25, 50, 100, 1000, 10,000-fold more) in a biological sample obtained from a patient having adrenomyeloneuropathy (AMN) than the amount of gene expression or protein expression in a biological sample obtained from a patient not having AMN. "Increased" as it refers to gene expression or protein expression also means at least about 5% more (for example 5, 6, 7, 8, 9, 10, 15, 20, 25, 30, 35, 40, 45, 50, 55, 60, 65, 70, 75, 80, 85, 90, 95, 99 or 100%) in a biological sample obtained from a patient having AMN than the amount of gene expression or protein expression in a subject not having AMN. Amounts can be measured according to methods known in the art for determining amounts of gene expression or protein expression.

As used herein "a decrease in expression" refers to an amount of gene expression or protein expression that is at least about 0.05 fold less (for example 0.1, 0.2, 0.3, 0.4, 0.5, 1, 5, 10, 25, 50, 100, 1000, 10,000-fold less) in a biological sample obtained from a patient having adrenomyeloneuropathy (AMN) than the amount of gene expression or protein expression in a biological sample obtained from a patient having childhood cerebral ALD (CALD). "Decreased" as it refers to gene expression or protein expression also means at least about 5% less (for example 5, 6, 7, 8, 9, 10, 15, 20, 25, 30, 35, 40, 45, 50, 55, 60, 65, 70, 75, 80, 85, 90, 95, 99 or 100% less) in a biological sample obtained from a patient having AMN than the amount of gene expression or protein expression in a subject having childhood cerebral ALD (CALD). Amounts can be measured according to methods known in the art for determining amounts of gene expression or protein expression.

As used herein, the term "reference level" refers to the level of expression of a biomarker in a known sample against which another test sample is compared. A reference level can be obtained, for example, from a known AMN or CALD positive sample from a different individual (e.g., not the individual being tested). A known sample can also be obtained by pooling samples from a plurality of individuals to produce a reference level over an averaged population. A "level" can be an amount of nucleic acid (gene, mRNA) expression or protein expression of a biomarker. Another type of reference level is a "control" which, as used herein in specific embodiments, refers to a level of expression of a biomarker in a sample obtained from a subject known not to have AMN (e.g., the subject is does not have aberrant mutations in the ABCDJ gene). In other specific embodiments, a "control" refers to a level of expression of a biomarker in a sample obtained from a subject known to have CALD (e.g., the subject does have aberrant mutations in the ABCDJ gene and a clinical diagnosis of CALD).

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

Other definitions appear in context throughout this disclosure.

Methods

Described herein are methods for diagnosing and treating adrenomyeloneuropathy (AMN) using biomarkers including, but not limited to, milk fat globule-EGF factor 8 (MFGE8), complement C1q A chain (C1qa), triggering receptor expressed on myeloid cells 2 (Trem2), growth arrest specific 6 (Gas6), tumor necrosis factor (TNF) alpha and interleukin 1 (ILI1) beta.

The human nucleotide and amino acid sequences encoding MFGE8 are known in the art and can be located, for example, at GenBank accession numbers NM_005928.3 and NP_005919.2, respectively. Antibodies for use in monitoring MFGE8 levels are also well known in the art and are described, for example, by Das, A., (2016) Correction of MFG-E8 Resolves Inflammation and Promotes Cutaneous Wound Healing in Diabetes. J. Immunol. 196 (12). Levels of MFGE8 are increased in human male subjects diagnosed with X-linked adrenoleukodystrophy (X-ALD) that are at least about 20 years of age and who have Adrenomyeloneuropathy (AMN) compared to reference levels or control levels.

The human nucleotide and amino acid sequences encoding C1qa are known in the art and can be located, for example, at GenBank accession numbers NM_015991.3 and NP_057075.1, respectively. Antibodies for use in monitoring C1qa levels are also well known in the art and are described, for example, by Hansen, L., (2016) Cell, 165 (4), pp. 921-935. Levels of C1qa are increased in human male subjects diagnosed with X-linked adrenoleukodystrophy (X-ALD) that are at least about 20 years of age and who have Adrenomyeloneuropathy (AMN) compared to reference levels or control levels.

The human nucleotide and amino acid sequences encoding Trem2 are known in the art and can be located, for example, at GenBank accession numbers NM_018965.3 and NP_061838.1, respectively. Antibodies for use in monitoring Trem2 levels are also well known in the art and are described, for example, by Wyatt, S. K., (2017) Experimental Neurology, 295 pp. 184-193. Levels of Trem2 are increased in human male subjects diagnosed with X-linked adrenoleukodystrophy (X-ALD) that are at least about 20 years of age and who have Adrenomyeloneuropathy (AMN) compared to reference levels or control levels.

The human nucleotide and amino acid sequences encoding Gas6 are known in the art and can be located, for example, at GenBank accession numbers NM_000820.3 and NP_000811.1, respectively. Antibodies for use in monitoring Gas6 levels are also well known in the art and are described, for example, by Wenni, L. (2017) Clinical and experimental Hypertension, 39(4) pp. 382-387. Levels of Gas6 are increased in human male subjects diagnosed with X-linked adrenoleukodystrophy (X-ALD) that are at least about 20 years of age and who have Adrenomyeloneuropathy (AMN) compared to reference levels or control levels.

The human nucleotide nucleotide and amino acid sequences encoding TNF alpha are known in the art and can be located, for example, at GenBank accession numbers NM_000594.3 and NP_000585.2 respectively. Antibodies for use in monitoring TNF alpha levels are also well known in the art and are described, for example, by Ohtori S. (2011) Eur Spine J. 20(6) pp. 942-946. Levels of TNF alpha are decreased in human male subjects diagnosed with X-linked adrenoleukodystrophy (X-ALD) that are at least about 20 years of age and who have Adrenomyeloneuropathy (AMN) compared to reference levels or control levels in human male subjects diagnosed with X-linked adrenoleukodystrophy (X-ALD) and who have manifested Childhood cerebral ALD, or CALD.

The human nucleotide nucleotide and amino acid sequences encoding ILI1 beta are known in the art and can be located, for example, at GenBank accession numbers NM_000576.2 and NP_000567.1 respectively. Antibodies for use in monitoring ILI1 beta levels are also known in the art and are described, for example, by Shi, L. M., (2017) Childs Nery Syst. 33(5):805-811. Levels of ILI1 beta are decreased in human male subjects diagnosed with X-linked adrenoleukodystrophy (X-ALD) that are at least about 20 years of age and who have Adrenomyeloneuropathy (AMN) compared to reference levels or control levels in human male subjects diagnosed with X-linked adrenoleukodystrophy (X-ALD) and who have manifested Childhood cerebral ALD, or CALD.

The present methods can be used to detect adrenomyeloneuropathy in human male subjects diagnosed with X-linked adrenoleukodystrophy by determining the level of MFGE8, C1qa, Trem2, Gas6 or any combination thereof, in a biological sample obtained from the spine of the subject, and determining that the level or levels are increased compared to a reference level or levels. The methods can further comprise determining the level of TNF alpha and ILI1 beta in the biological sample or another sample obtained from the spine of a subject, wherein said level or levels are decreased compared to a reference level or levels, thereby determining that the patient does not have childhood cerebral ALD. The term "any combination thereof" means that any combination of the biomarkers (e.g., MFGE8, C1qa, Trem2, and Gas6) can be evaluated together, in addition to evaluating any single biomarker alone. In specific embodiments, MFGE8 is evaluated in combination with any one or more of the other biomarkers (e.g., C1qa, Trem2, and Gas6). Biological samples used in the methods can include, but are not limited to, biopsies of spinal tissue and spinal fluid.

Determining the level of one or more biomarkers can involve measuring an amount of mRNA or protein expression using methods known in the art.

To measure protein expression in general, a western blotting technique can be employed. In this regard, a predetermined amount of protein obtained from a biological sample is loaded on SDS PAGE gel, transferred onto a membrane, and reacted with an antibody with known antigenic specificity to a biomarker, and then, exposed using enhanced chemiluminescence, infrared-based, or alternative methodologies for the detection of a band. Band intensities can be determined by densitometry using commercially or publicly available software well known in the art.

In specific embodiments, an increased or decreased level of immunostaining in a sample is a level of immunostaining that would be considered higher or lower, respectively, than the level of immunostaining compared to a reference (e.g., control) by a person of ordinary skill in the art. Methods of immunostaining (also referred to as immunohistochemistry or IHC) are well known in the art.

Immunohistochemical (IHC) staining techniques are used for the visualization of antigens (e.g., anti-MFGE8) in tissue sections. These techniques are based on the immunoreactivity and specificity of antibodies, and the chemical properties of enzymes or enzyme complexes which react with colorless substrate-chromogens to produce a colored end product. IHC staining techniques include direct and indirect methods, either of which can be used. In the direct method, the chromogen is conjugated directly to an antibody with known antigenic specificity (primary antibody). This technique allows the visualization of tissue antigens using standard light microscopy. Commercial antibodies with known antigenic specificity to each of the biomarkers described herein are available, e.g., from Cell Signaling Technologies as well as other sources.

The indirect method is a two-step method in which enzyme-labeled secondary antibodies react with the antigen-bound primary antibody. Enzyme pairs which can be used in the indirect method include peroxidase-antiperoxidase (PAP) and avidin-biotin. When the indirect method employs an avidin-biotin complex (ABC), a biotinylated secondary antibody forms a complex with peroxidase-conjugated streptavidin molecules. Specimens are incubated with a primary antibody, followed by sequential incubations with the biotinylated secondary link antibody and peroxidase labeled streptavidin. The primary antibody-secondary antibody-avidin enzyme complex is then visualized utilizing a substrate-chromogen that produces a brown pigment at the antigen site that is visible by light microscopy.

Determining the amount of biomarker present in a test sample using IHC is done in comparison to a control sample (e.g., providing a "reference level"), using either manual scoring or automated detection systems. A spectrophotometric plate reader may be used for colorimetric detection. Several types of reporters can detect sensitivity in an immunoassay. For example, chemiluminescent substrates have been developed which further amplify the signal and can be read on a luminescent plate reader.

In other specific embodiments, biomarkers are detected using antibody-coated microbeads, such as magnetic beads. Alternatively, the beads are internally color-coded with fluorescent dyes and the surface of the bead is tagged with an anti-biomarker marker antibody (e.g., an anti-MFGE8 antibody) that can bind a biomarker in a test sample. The biomarker, in turn, is either directly labeled with a fluorescent tag or indirectly labeled with an anti-marker antibody conjugated to a fluorescent tag. Hence, there are two sources of color, one from the bead and the other from the fluorescent tag. Alternatively, the beads can be internally coded by different sizes.

By using a blend of different fluorescent intensities from the two dyes, as well as beads of different sizes, the assay can measure up to hundreds of different cancer markers. During the assay, a mixture containing the color/size-coded beads, fluorescence labeled anti-marker antibodies, and sample are combined and injected into an instrument that uses precision fluidics to align the beads. The beads then pass through a laser and, on the basis of their color or size, either get sorted or measured for color intensity, which is processed into quantitative data for each reaction.

When samples are directly labeled with fluorophores, the system can read and quantitate only fluorescence on beads without removing unbound fluorophores in solution. The assays can be multiplexed by differentiating various colored or sized beads. Real time measurement is achievable when a sample is directly required for unlabeled samples. Standard assay steps include incubation of a sample with anti-biomarker antibody coated beads, incubation with biotin or fluorophore-labeled secondary antibody, and detection of fluorescence signals. Fluorescent signals can be developed on bead (by adding streptavidin-fluorophore conjugates for biotinylated secondary antibody) and read out by a bead analyzer. Depending on the anti-biomarker immobilized on the bead surface, a bead-based immunoassay can be a sandwich type or a competitive type immunoassay.

In other specific embodiments, the biomarkers are detected by a protein microarray containing immobilized biomarker-specific antibodies on its surface. The microarray can be used in a "sandwich" assay in which the antibody on the microarray captures a biomarker in the test sample and the captured biomarker is detected by a labeled secondary antibody that specifically binds to the captured biomarker. The secondary antibody can be biotinylated or enzyme-labeled. The detection is achieved by subsequent incubation with a streptavidin-fluorophore conjugate (for fluorescence detection) or an enzyme substrate (for colorimetric detection).

Typically, a microarray assay contains multiple incubation steps, including incubation with the samples and incubation with various reagents (e.g., primary antibodies, secondary antibodies, reporting reagents, etc.). Repeated washes are also needed between the incubation steps. In some embodiments, the microarray assays is performed in a fast assay mode that requires only one or two incubations. It is also conceivable that the formation of a detectable immune complex (e.g., a captured biomarker/anti-biomarker antibody/label complex) may be achieved in a single incubation step by exposing the protein microarray to a mixture of the sample and all the necessary reagents. In some embodiments, the primary and secondary antibodies are the same antibody.

In another specific embodiment, the protein microarray provides a competitive immunoassay. Briefly, a microarray comprising immobilized anti-biomarker antibodies is incubated with a test sample in the presence of a labeled biomarker standard. The labeled biomarker competes with the unlabeled biomarker in the test sample for the binding to the immobilized antigen-specific antibody. In such a competitive setting, an increased concentration of the specific biomarker in the test sample would lead to a decreased binding of the labeled biomarker standard to the immobilized antibody and hence a reduced signal intensity from the label.

The microarray can be processed in manual, semi-automatic or automatic modes. Manual mode refers to manual operations for all assay steps including reagent and sample delivery onto microarrays, sample incubation and microarray washing. Semi-automatic modes refer to manual operation for sample and reagent delivery onto microarray, while incubation and washing steps operate automatically. In an automatic mode, three steps (sample/reagent delivery, incubation and washing) can be controlled by a computer or an integrated breadboard unit with a keypad. For example, the microarray can be processed with a ProteinArray Workstation (PerkinElmer Life Sciences, Boston, Mass.). Scanners by fluorescence, colorimetric and chemiluminescence, can be used to detect microarray signals and capture microarray images. Quantitation of microarray-based assays can also be achieved by other means, such as mass spectrometry and surface plasma resonance. Captured microarray images can be analyzed by stand-alone image analysis software or with image acquisition and analysis software package.

In other specific embodiments, the cancer markers are detected using mass spectrometry (MS) such as MALDI/TOF (time-of-flight), SELDI/TOF, liquid chromatography-mass spectrometry (LC-MS), gas chromatography-mass spectrometry (GC-MS), high performance liquid chromatography-mass spectrometry (HPLC-MS), capillary electrophoresis-mass spectrometry, nuclear magnetic resonance spectrometry, or tandem mass spectrometry (e.g., MS/MS, MS/MS/MS, ESI-MS/MS, etc.).

Mass spectrometry methods are well known in the art and have been used to quantify and/or identify biomarkers, such as proteins. Further, mass spectrometric techniques have been developed that permit at least partial de novo sequencing of isolated proteins. In certain embodiments, a gas phase ion spectrophotometer is used. In other embodiments, laser-desorption/ionization mass spectrometry is used to analyze the sample. Modern laser desorption/ionization mass spectrometry ("LDI-MS") can be practiced in two main variations: matrix assisted laser desorption/ionization ("MALDI") mass spectrometry and surface-enhanced laser desorption/ionization ("SELDI"). In MALDI, the analyte is mixed with a solution containing a matrix, and a drop of the liquid is placed on the surface of a substrate. The matrix solution then co-crystallizes with the biological molecules. The substrate is inserted into the mass spectrometer. Laser energy is directed to the substrate surface where it desorbs and ionizes the biological molecules without significantly fragmenting them. In SELDI, the substrate surface is modified so that it is an active participant in the desorption process. In some embodiments, the surface is derivatized with adsorbent and/or capture reagents that selectively bind the protein of interest. In another embodiment, the surface is derivatized with energy absorbing molecules that are not desorbed when struck with the laser. In another embodiment, the surface is derivatized with molecules that bind the protein of interest and that contain a photolytic bond that is broken upon application of the laser. In each of these methods, the derivatizing agent generally is localized to a specific location on the substrate surface where the sample is applied. See, e.g., U.S. Pat. No. 5,719,060 (Hutchens & Yip) and WO 98/59361 (Hutchens & Yip). The two methods can be combined by, for example, using a SELDI affinity surface to capture an analyte and adding matrix-containing liquid to the captured analyte to provide the energy absorbing material.

Detection of the presence of a biomarker will typically involve detection of signal intensity. This, in turn, can reflect the quantity and character of a polypeptide bound to the substrate. For example, in certain embodiments, the signal strength of peak values from spectra of a first sample and a second sample can be compared (e.g., visually, by computer analysis etc.), to determine the relative amounts of particular biomarkers. Software programs can be used to aid in analyzing mass spectra. The mass spectrometers and their techniques are well known to those of skill in the art.

A person skilled in the art understands that any of the components of a mass spectrometer (e.g., desorption source, mass analyzer, detect, etc.) and varied sample preparations can be combined with other suitable components or preparations described herein, or to those known in the art. For example, in some embodiments a control sample may contain heavy atoms (e.g. 13C) thereby permitting the test sample to be mixed with the known control sample in the same mass spectrometry run.

In other specific embodiments, expression of the biomarker(s) is determined at the mRNA level by quantitative RT-PCR (with or without laser capture microdissection of cancer cells), in situ hybridization, Northern blot, gene microarray, RNAseq, or other methods known to a person of ordinary skill in the art.

RT-PCR involves a single-stranded RNA of a biomarker, which comprises the sequence to be amplified (e.g., an mRNA or portion thereof of a biomarker), and can be incubated in the presence of a reverse transcriptase, two primers, a DNA polymerase, and a mixture of dNTPs suitable for DNA synthesis. mRNA sequences of the biomarkers described herein are well known in the art. During this process, one of the primers anneals to the RNA target and can be extended by the action of the reverse transcriptase, yielding an RNA/cDNA doubled-stranded hybrid. This hybrid can be then denatured and the other primer anneals to the denatured cDNA strand. Once hybridized, the primer can be extended by the action of the DNA polymerase, yielding a double-stranded cDNA, which then serves as the double-stranded target for amplification through PCR. RT-PCR amplification reactions can be carried out with a variety of different reverse transcriptases, and in various embodiments, a thermostable reverse-transcriptions can be used. Quantitative RT-PCR involves amplifying an internal control simultaneously with the biomarker sequence of interest. The internal control is used to normalize the samples. Once normalized, direct comparisons of relative abundance of a specific mRNA can be made across the samples. Commonly used internal controls include, for example, GAPDH, HPRT, actin and cyclophilin.

In other aspects, methods described herein enable a treating physician to select a treatment that is specific for the manifested phenotype of the X-ALD male subject (e.g., AMN but not CALD, AMD and CALD, or CALD but not AMN) and correlated with a good clinical response. For example, if the subject has AMN but not CALD, the treatment is specific for AMN and comprises, for example, phosphatidylserine exposure, inhibiting MFGE8, and/or inhibiting the microglial vitronectin receptor. If the subject also has CALD, additional treatments known in the art can be administered, including but not limited to hematopoetic stem cell transplantation. Additional details regarding treatments are known in the art; see, e.g., Engelen et al., Orphanet J Rare Dis. 2012; 7: 51; Moser H W. Adrenoleukodystrophy: phenotype, genetics, pathogenesis and therapy. Brain 1997; 120:1485-508; Mosser J, Lutz Y, Stoeckel M E et al. The gene responsible for adrenoleukodystrophy encodes a peroxisomal membrane protein. Hum Mol Genet 1994; 3:265-71; Engelen M, Kemp S, de Visser M et al. X-linked adrenoleukodystrophy (X-ALD): clinical presentation and guidelines for diagnosis, follow-up and management. Orphanet J Rare Dis 2012; 7:51; Berger J, Pujol A, Aubourg P et al. Current and future pharmacological treatment strategies in X-Linked adrenoleukodystrophy. Brain Pathol 2010; 20:845-56; Köhler W, Kühl J. Hematopoietic stem cell transplantation for adult cerebral X-linked adrenoleukodystrophy. Neurology 2014; 82:5.174; Hitomi T, Mezaki T, Tomimoto H et al. Long-term effect of bone marrow transplantation in adult-onset adrenoleukodystrophy. Eur J Neurol 2005; 12:807-10; Moser H. Clinical and therapeutic aspects of adrenoleukodystrophy and adrenomyeloneuropathy. J Neuropathol Exp Neurol 1995; 54:740-5; Patel and Gutowski, BMJ Case Rep. 2015; 2015: bcr2015209732, all of which are incorporate herein in their entirety.

In other aspects, the present methods are directed to the treatment of AMN. In some embodiments, treatments for AMN comprise administering an anti-MFGE8 antibody or antigen-binding portion thereof to a human male subject diagnosed with X-ALD in an amount and duration sufficient to alleviate or improve abnormalities in balance and/or gait and/or abnormal bladder functions, thereby treating, thereby treating adrenomyeloneuropathy in the human male subject. Humanized anti-MFGE8 antibody is known in the art and is available, for example, from Sigma-Aldrich Catalog Number 12136.

The term "antibody" as used herein refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments the antibody has effector function and can fix complement. In some embodiments, the antibody has reduced or no ability to bind an Fc receptor. For example, the antibody can be an isotype or subtype, fragment or other mutant, which does not support binding to an Fc receptor, e.g., it has a mutagenized or deleted Fc receptor binding region. Methods for making antibodies and fragments thereof are known in the art, see, e.g., Harlow et. al., editors, Antibodies: A Laboratory Manual (1988); Goding, Monoclonal Antibodies: Principles and Practice, (N.Y. Academic Press 1983); Howard and Kaser, Making and Using Antibodies: A Practical Handbook (CRC Press; 1st edition, Dec. 13, 2006); Kontermann and Dithel, Antibody Engineering Volume 1 (Springer Protocols) (Springer; 2nd ed., May 21, 2010); Lo, Antibody Engineering: Methods and Protocols (Methods in Molecular Biology) (Humana Press; Nov. 10, 2010); and Dithel, Handbook of Therapeutic Antibodies: Technologies, Emerging Developments and Approved Therapeutics, (Wiley-VCH; 1 edition Sep. 7, 2010).

The dosage range for the administered therapy depends upon the potency, and includes amounts large enough to produce the desired effect, e.g., cellular differentiation or treatment of cancer. The dosage should not be so large as to cause unacceptable adverse side effects. Generally, the dosage will vary with the type of inhibitor (e.g., an antibody or fragment, small molecule, siRNA, etc.), and with the age, condition, and sex of the patient. The dosage can be determined by one of skill in the art and can also be adjusted by the individual physician in the event of any complication.

Typically, the dosage ranges from 0.001 mg/kg body weight to 5 g/kg body weight. In some embodiments, the dosage range is from 0.001 mg/kg body weight to 1 g/kg body weight, from 0.001 mg/kg body weight to 0.5 g/kg body weight, from 0.001 mg/kg body weight to 0.1 g/kg body weight, from 0.001 mg/kg body weight to 50 mg/kg body weight, from 0.001 mg/kg body weight to 25 mg/kg body weight, from 0.001 mg/kg body weight to 10 mg/kg body weight, from 0.001 mg/kg body weight to 5 mg/kg body weight, from 0.001 mg/kg body weight to 1 mg/kg body weight, from 0.001 mg/kg body weight to 0.1 mg/kg body weight, from 0.001 mg/kg body weight to 0.005 mg/kg body weight. Alternatively, in some embodiments the dosage range is from 0.1 g/kg body weight to 5 g/kg body weight, from 0.5 g/kg body weight to 5 g/kg body weight, from 1 g/kg body weight to 5 g/kg body weight, from 1.5 g/kg body weight to 5 g/kg body weight, from 2 g/kg body weight to 5 g/kg body weight, from 2.5 g/kg body weight to 5 g/kg body weight, from 3 g/kg body weight to 5 g/kg body weight, from 3.5 g/kg body weight to 5 g/kg body weight, from 4 g/kg body weight to 5 g/kg body weight, from 4.5 g/kg body weight to 5 g/kg body weight, from 4.8 g/kg body weight to 5 g/kg body weight. In some embodiments, the dose range is from 5 ug/kg body weight to 30 ug/kg body weight. Alternatively, the dose range will be titrated to maintain serum levels between 5 ug/mL and 30 ug/mL.

Administration of the doses recited above can be repeated for a limited period of time. In some embodiments, the doses are given once a day, or multiple times a day, for example but not limited to three times a day. In a preferred embodiment, the doses recited above are administered daily for several weeks or months. The duration of treatment depends upon the subject's clinical progress and responsiveness to therapy. Continuous, relatively low maintenance doses are contemplated after an initial higher therapeutic dose.

A therapeutically effective amount is an amount of an agent that is sufficient to produce a statistically significant, measurable change in immune response (see "Efficacy Measurement" below). Such effective amounts can be gauged in clinical trials as well as animal studies for a given agent.

Agents useful in the methods and compositions described herein can be administered topically, intravenously (by bolus or continuous infusion), orally, by inhalation, intraperitoneally, intramuscularly, subcutaneously, intracavity, and can be delivered by peristaltic means, if desired, or by other means known by those skilled in the art. The agent can be administered systemically, if so desired.

Therapeutic compositions containing at least one agent can be conventionally administered in a unit dose. The term "unit dose" when used in reference to a therapeutic composition refers to physically discrete units suitable as unitary dosage for the subject, each unit containing a predetermined quantity of active material calculated to produce the desired therapeutic effect in association with the required physiologically acceptable diluent, i.e., carrier, or vehicle.

The compositions are administered in a manner compatible with the dosage formulation, and in a therapeutically effective amount. The quantity to be administered and timing depends on the subject to be treated, capacity of the subject's system to utilize the active ingredient, and degree of therapeutic effect desired. An agent can be targeted by means of a targeting moiety, such as e.g., an antibody or targeted liposome technology. In some embodiments, an agent can be targeted to a tissue by using bispecific antibodies, for example produced by chemical linkage of an anti-ligand antibody (Ab) and an Ab directed toward a specific target. To avoid the limitations of chemical conjugates, molecular conjugates of antibodies can be used for production of recombinant bispecific single-chain Abs directing ligands and/or chimeric inhibitors at cell surface molecules. The addition of an antibody to an agent permits the agent to accumulate additively at the desired target site (e.g., a tumor). Antibody-based or non-antibody-based targeting moieties can be employed to deliver a ligand or the inhibitor to a target site. Preferably, a natural binding agent for an unregulated or disease associated antigen is used for this purpose.

Precise amounts of active ingredient required to be administered depend on the judgment of the practitioner and are particular to each individual. However, suitable dosage ranges for systemic application are disclosed herein and depend on the route of administration. Suitable regimes for administration are also variable, but are typified by an initial administration followed by repeated doses at one or more intervals by a subsequent injection or other administration. Alternatively, continuous intravenous infusion sufficient to maintain concentrations in the blood in the ranges specified for in vivo therapies are contemplated.

The present invention is additionally described by way of the following illustrative, non-limiting Examples that provide a better understanding of the present invention and of its many advantages.

EXAMPLES

The following Examples illustrate some embodiments and aspects of the invention. It will be apparent to those skilled in the relevant art that various modifications, additions, substitutions, and the like can be performed without altering the spirit or scope of the invention, and such modifications and variations are encompassed within the scope of the invention as defined in the claims that follow. The following Examples do not in any way limit the invention.

Example 1. Microglial Activation Precedes Synapse Loss in the Spinal Cord of Aging Abcd1−/− Mice The aim of the present study was to systematically define microglia in human and mouse spinal cord and to further explore dysfunction of ABCD1-deficient microglia both in vivo and in vitro. Abcd1−/− mice develop an AMN-like phenotype at an advanced age (Pujol et al., 2002). Synapse loss has long been considered an integral aspect of neurodegeneration. Hence, the time course of axon degeneration and microglial activation in spinal cord was examined in Abcd1−/− mice. Wild type C57BL/6 and congenic C57BL/6 Abcd1−/− mice were obtained from the Jackson laboratory. Abcd1−/− mice were backcrossed onto a pure C57/B6 background over 6 generations. They were then bred from homozygous founders, and occasionally genotyped. Mice were fed a standard diet and maintained under a 12-hour light-dark cycle. Only male mice were used for the experiments. For Western blotting, tissue was prepared using RIPA buffer (Sigma-Aldrich) with 1% Halt Protease and Phosphatase Inhibitor Cocktail (Roche). Protein samples were separated on NuPAGE 4-12% Bis-tris gels (Life science technologies) and transferred onto PVDF membranes (Millipore). Membranes were blocked with 5% non-fat milk in PBS containing 0.05% Tween 20 and probed with antibodies against iNOS, Cox2 (Santa Cruz), ABCD1, C1q, PSD95 and CD11b (Abcam), synaptophysin (Cell signaling), MFGE8 (MBL International), IBA1 (Wako), Beta-actin or GADPH (Santa Cruz) were used as protein loading control. Membranes were developed with SuperSignal West Pico Chemiluminescent Substrate (Thermo) after incubation with HRP-conjugated second antibodies. Antibodies that differed in human specimen included anti-human MFGE8 (Sigma-Aldrich) and anti-human ABCD1 (Origene, Rockville, MD). For immunofluorescence staining and confocal microscopy imaging, spinal cord sections (14 μm) were cut at −25° C. using cryostat (Leica) and permeabilized in blocking buffer containing 0.3% Triton X and 2% goat serum for 1 hour. Sections were then stained with IBA1 (Wako), CD68 (Bio-Rad for mouse and Abcam for human), synaptophysin (Sigma), C1q (Abcam), Neurofilament and NeuN (Abcam) antibodies respectively.

As early as 8 months prior to synapse loss, the spinal cord microglia of Abcd1−/− mice display an enlarged soma and upregulated CD68 expression (FIGS. 1A-1E). This activation of Abcd1−/− microglia coincided with them enveloping synapses and axons, suggesting that microglia are actively contributing to axonal degeneration (FIGS. 2A-2F). Importantly, vessel walls were intact and no significant monocytic activation was seen around the vessel, indicating that innate immune activation in AMN mice is largely due to resident microglia alone.

Figure 1A:
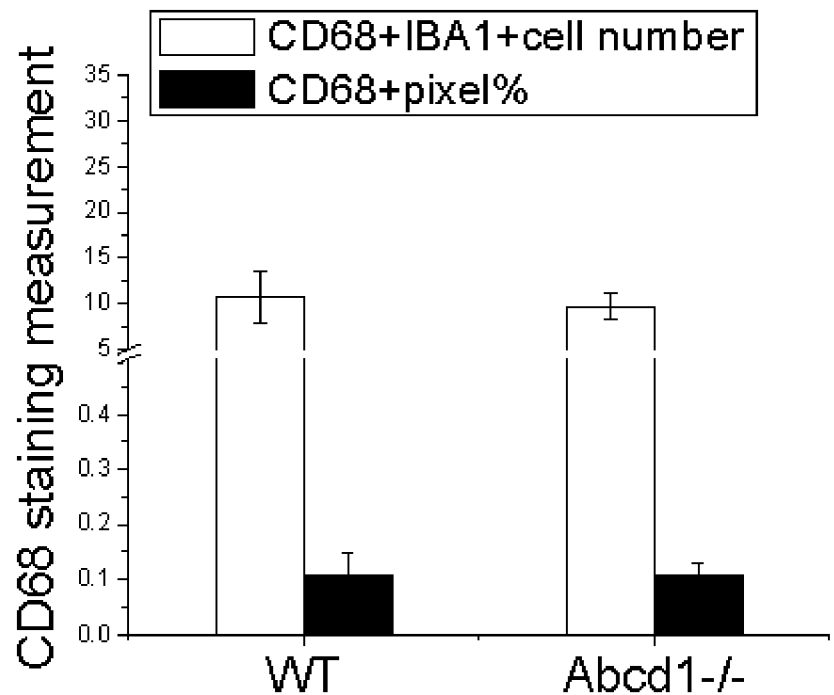
FIGS. 1A-1E depict the expression level of microglia activation marker at different ages in Abcd1−/− mouse spinal cord. (A) In 2 month old mouse spinal cord, resident microglia are quiescent with thin processes, while no significant change of CD68 expression in IBA1 positive microglia was detected, indicating a lack of microglia activation at this stage (n=4). (B) In 8 month old Abcd1−/− mouse spinal cord, microglia had relatively increased soma size and upregulated CD68 expression compared to wild type, indicating microglial activation (n=6). (C) In 15 month old Abcd1−/− mouse spinal cord, microglia had enlarged soma size as well as thick and bushy processes (see magnification, white arrow). Significant increases of CD68 in IBA1+ microglia were also detected (n=8). Bar=50 μm. CD68+ pixels and CD68+IBA1+cell number were quantified by Image." (D) Representative western blot shows IBA1 expression in spinal cord across different ages and (E) IBA1 protein quantification using Image J with b-actin as a loading control. Data were expressed as mean±SEM, *P<0.05, **P<0.01.
Figure 1B:
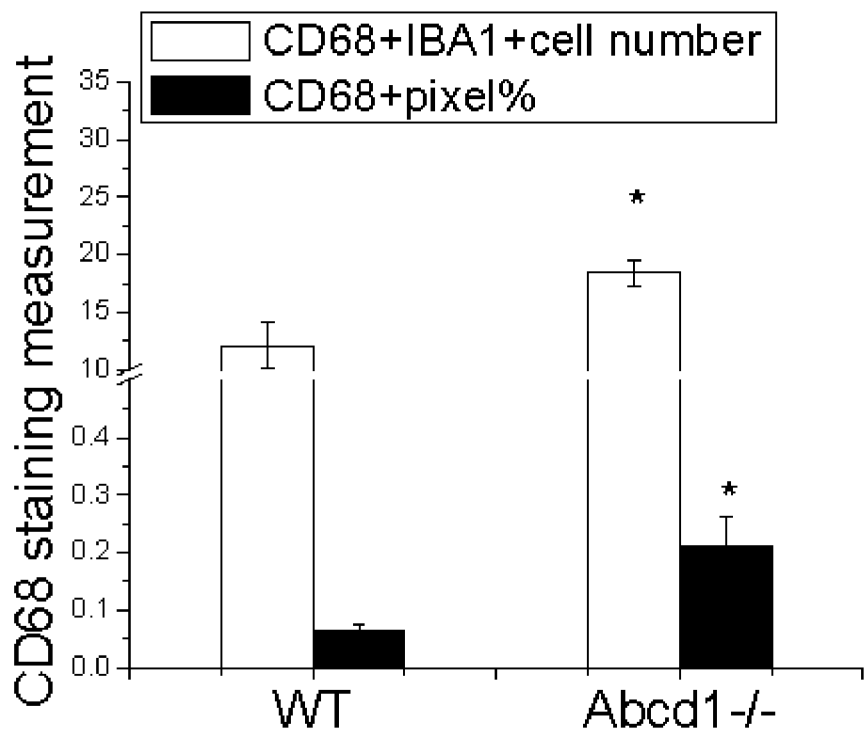
Figure 1C:
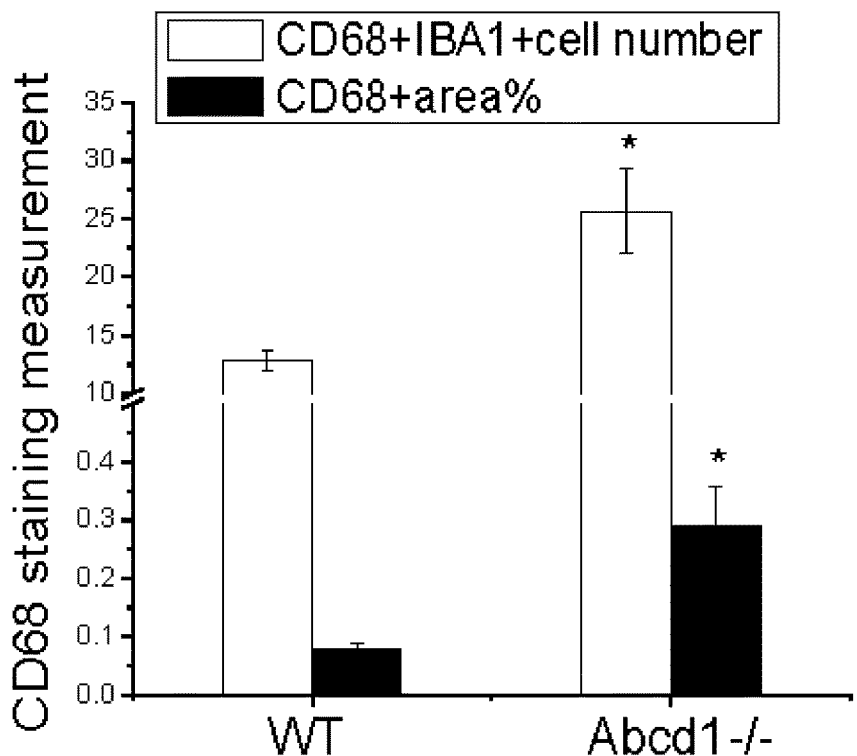
Figure 1D:
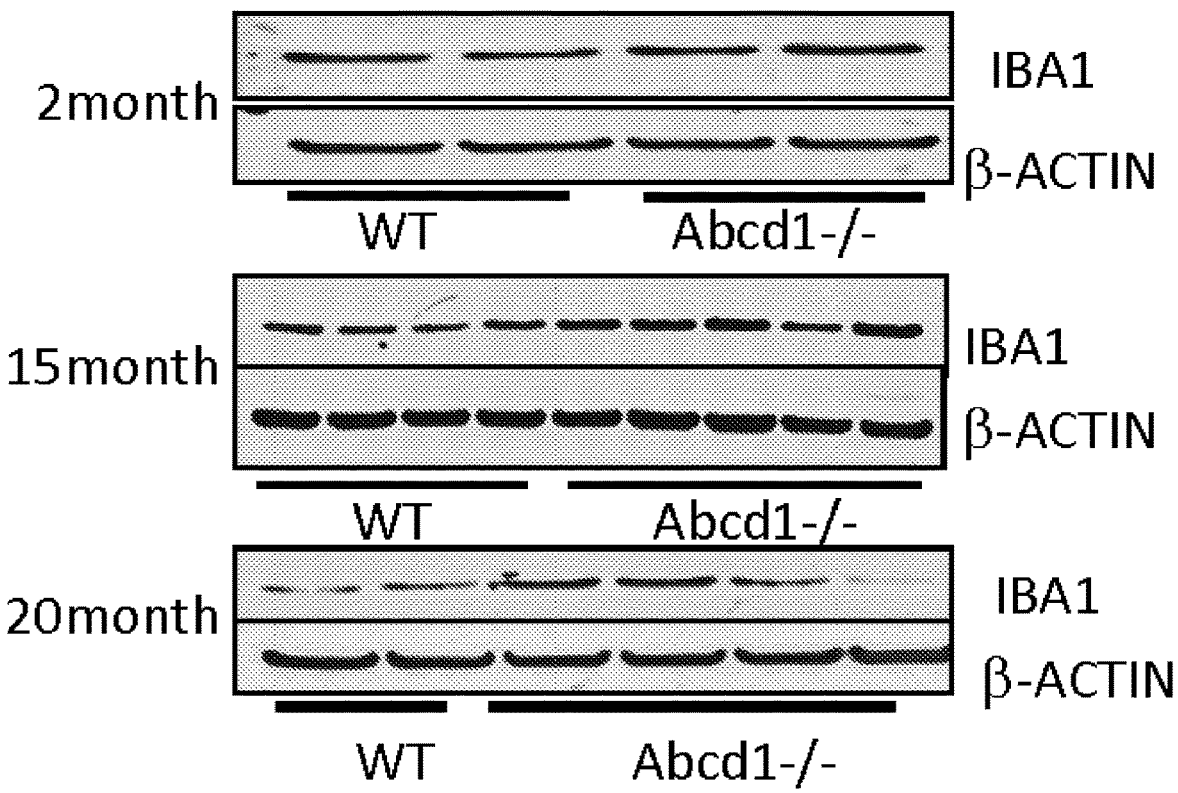
Figure 1E:
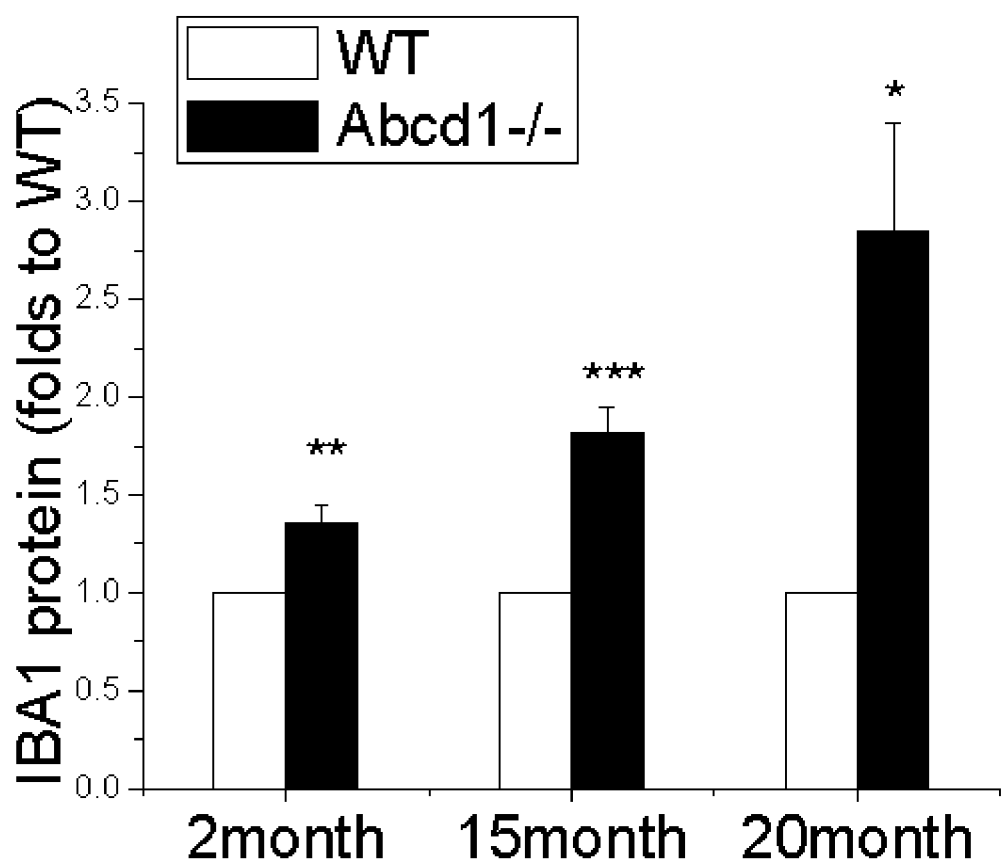
Figure 2A:
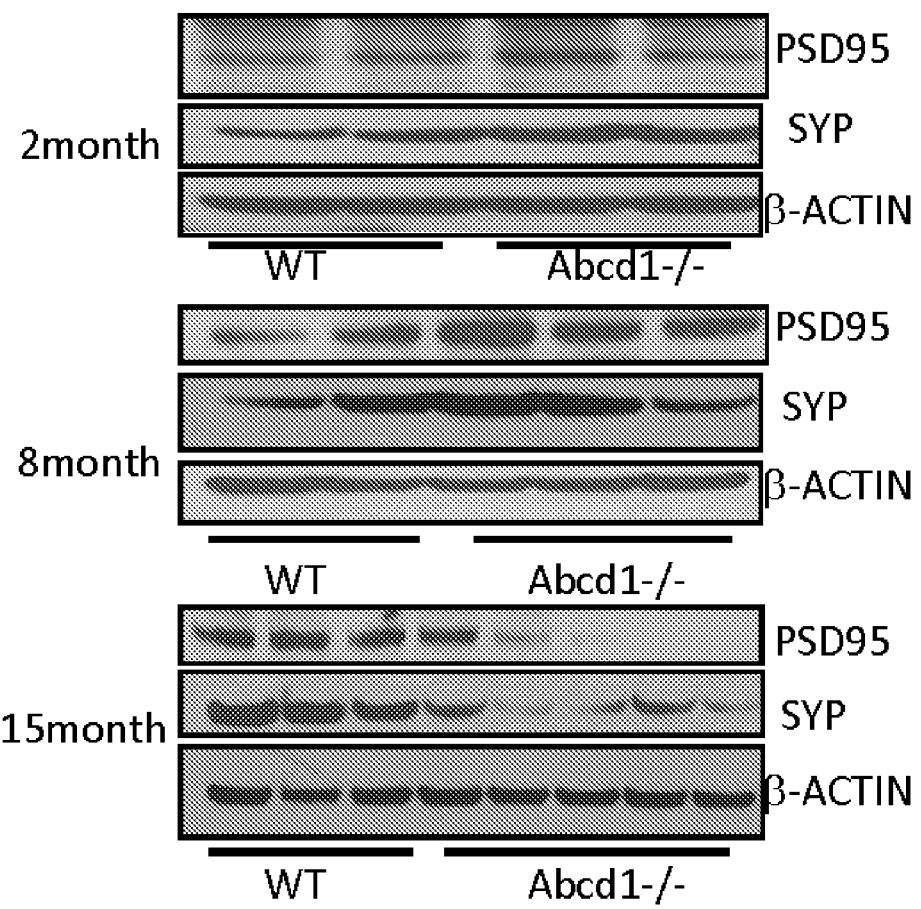
FIGS. 2A-2F depicts the presence of synapse loss, a marker of axon degeneration at different ages in Abcd1−/− mice spinal cord. (A) Representative western blot showed presynaptic synaptophysin and postsynaptic PSD95 expression in Abcd1−/− spinal cord across different age and (B) synaptophysin as well as (C) PSD95 protein quantification using Image J with beta-actin as loading control (n=12). (D) Synaptophysin (SYP) gene and (E) PSD95 (DLG4) gene expression in Abcd1−/− spinal cord at different ages (n=4 at 2 month and n=12 at 15 month) are shown. Co-staining of IBA1 and NeuN showed activated microglia surrounding neurons in 15 month old Abcd1−/− mouse spinal cord. (F) Immunofluorescence quantification of synaptophysin pixels in 15 month old spinal cord using image J (n=7) is shown. 3D confocal images showed microglia (CD68) engulfing synapses (synaptophysin) in 15 month old mouse spinal cord. In wild type spinal cord more punctate synaptophysin staining was present compared to the Abcd1−/− spinal cord where synapse loss occurs. Data were expressed as mean±SEM, *P<0.05, ***P<0.001.
Figure 2B:
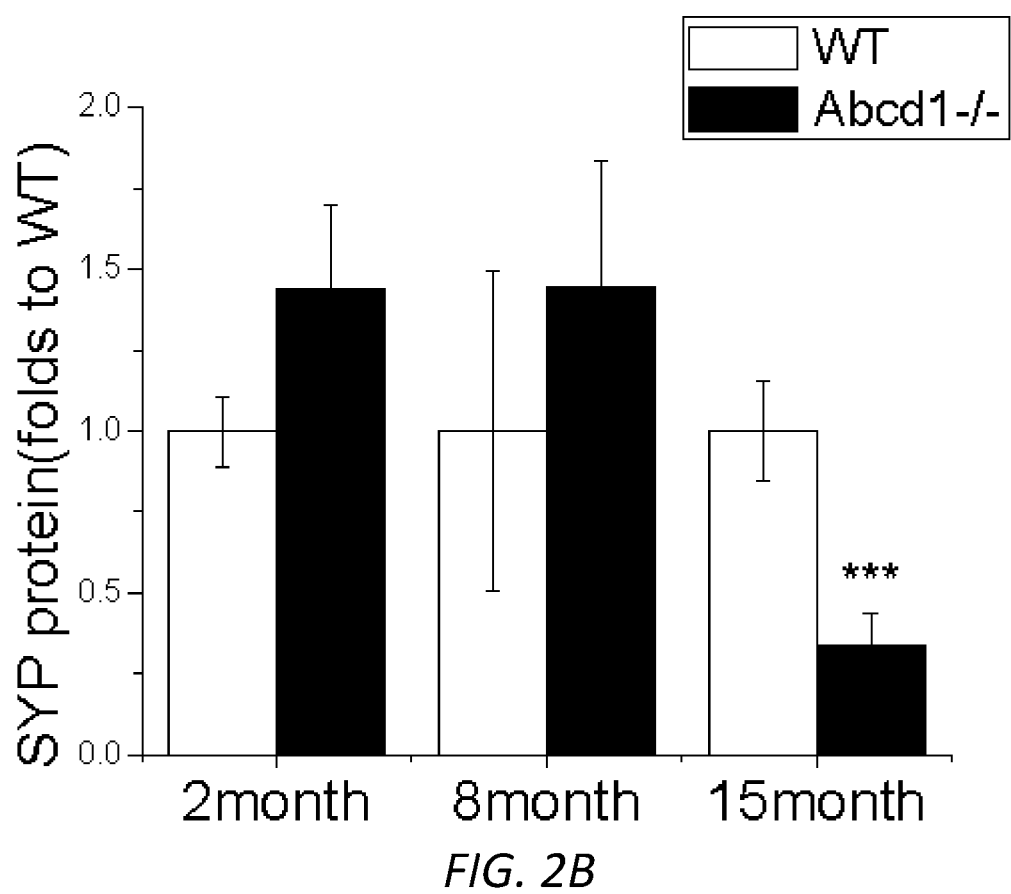
Figure 2C:
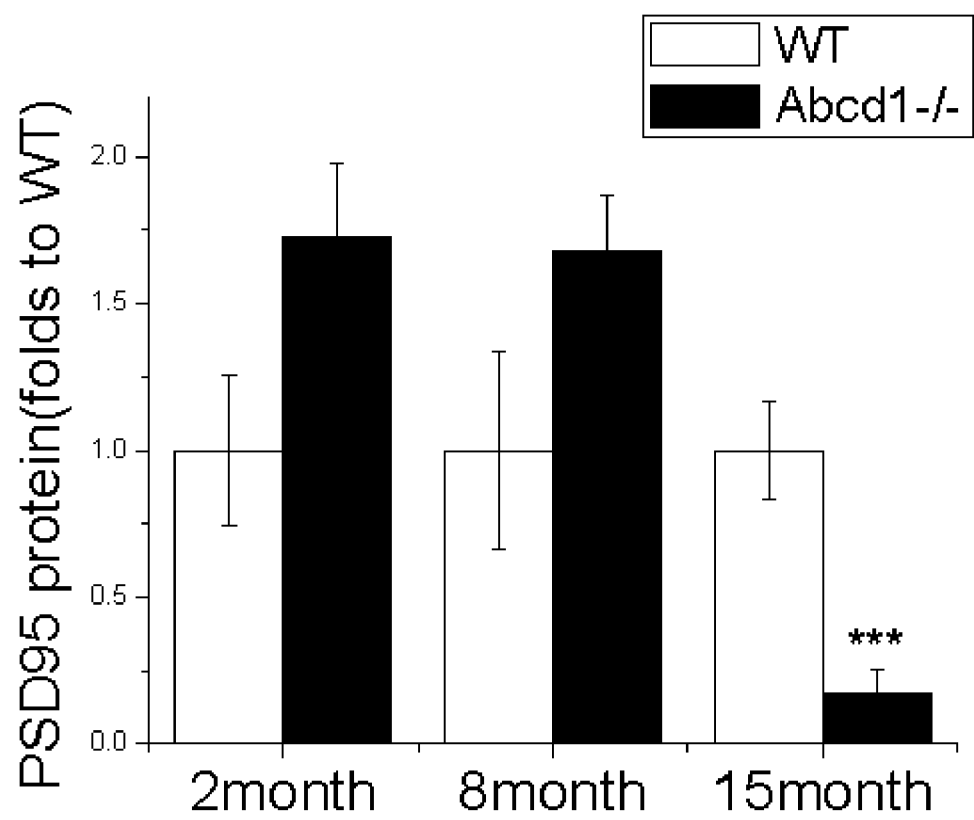
Figure 2D:
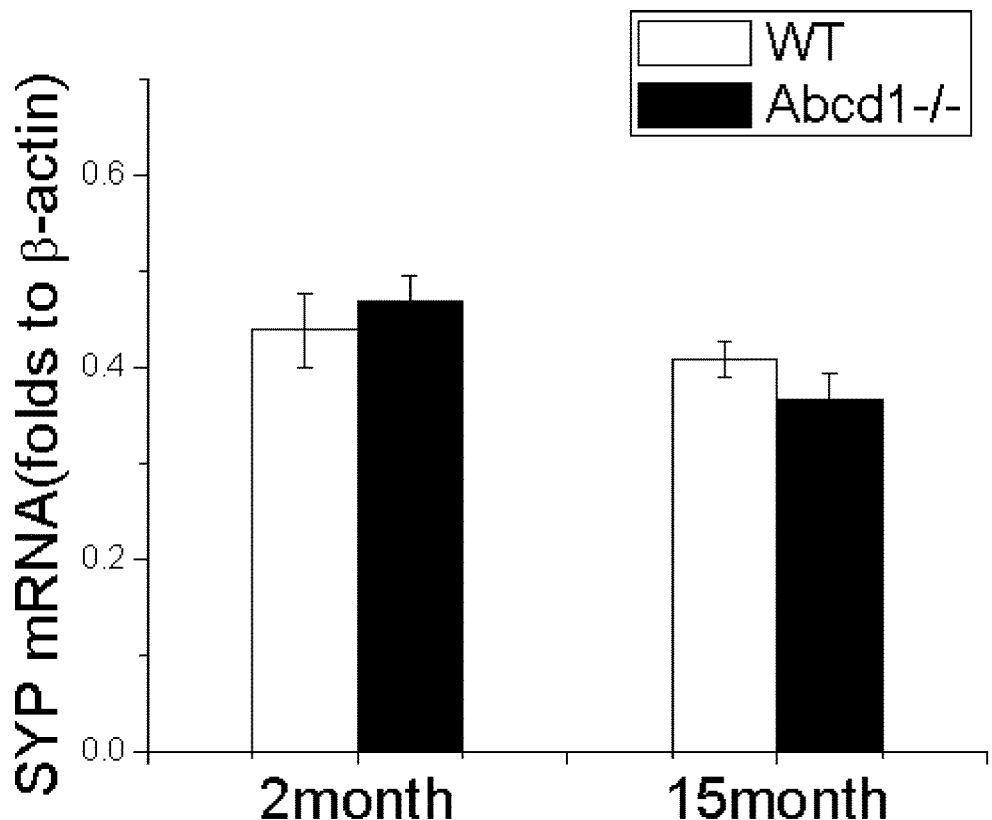
Figure 2E:
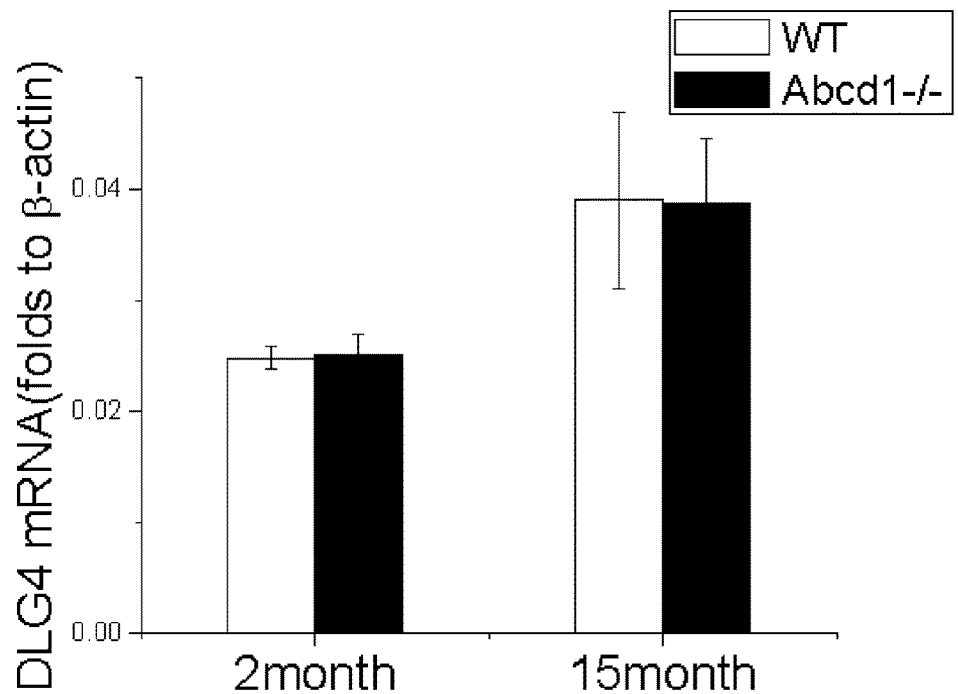
Figure 2F:
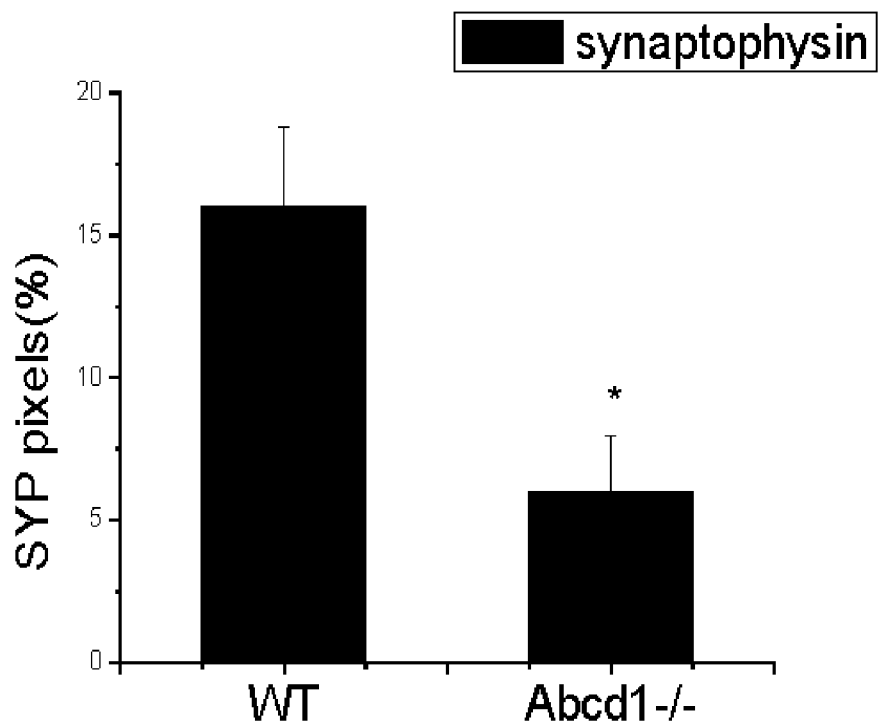
Figure 3A:
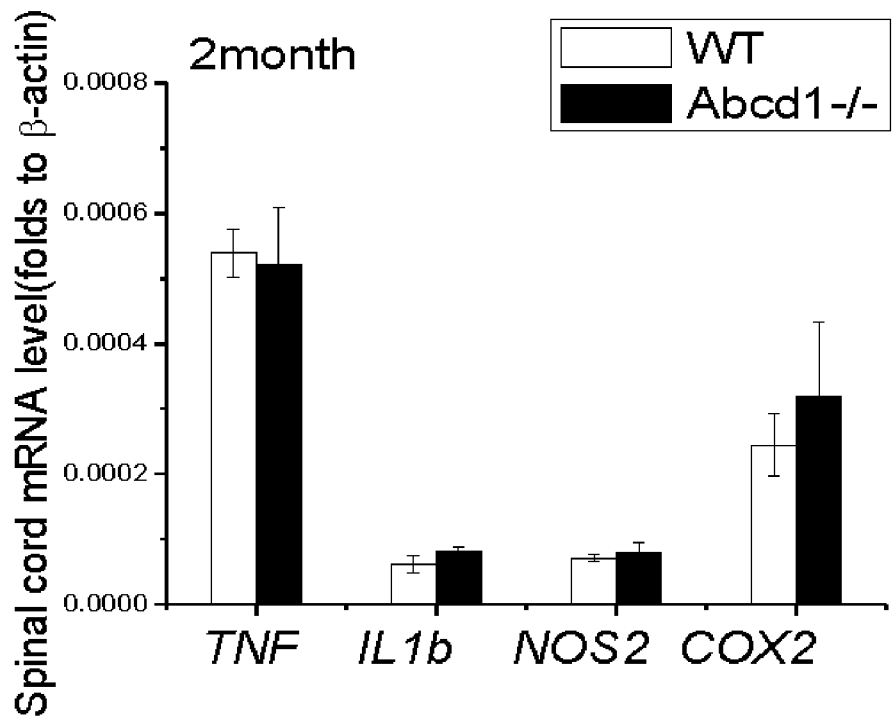
FIGS. 3A-3K depicts unaltered proinflammatory gene but increased phagocytosis related gene expression in spinal cord of Abcd1−/− mice at different ages. (A) The expression of proinflammatory genes including TNFa, IL1b, NOS2 and Cox2 in spinal cord of 2 month old wild type and Abcd1−/− mice is shown. (n=4) (B) The expression of proinflammatory genes including TNFa, IL1b, NOS2 and Cox2 in the spinal cord of 15 month old wild type and Abcd1−/− mice (n=5) is shown. (C) Western blot analysis of iNOS expression in 2 month (n=4) and 20 month old (n=4) spinal cord is shown. (D) Phagocytosis related genes expression including Trem2, MFGE8, Gas6, Bai1 C1qa and C3 in the spinal cord of 2 month old mice wild type and Abcd1−/− mice (n=4) is shown. (E) Representative western blot images show protein expression of MFGE8 and Trem2 in 2 month old mouse spinal cord. (F) Quantification of protein expression in 2 month old mouse spinal cord with beta-actin as loading control (n=4) shown. (G) Phagocytosis related gene expression including Trem2, MFGE8, Gas6, Bai1 C1qa and C3 in the spinal cord of 15 month old wild type and Abcd1−/− mice (n=12) is shown. (H) Representative western blot image shows protein expression of MFGE8, Trem2 and C1q in 15 month old mouse spinal cord. (I) Quantification of protein expression in 15 month old mouse spinal cord with beta-actin as loading control (n=12). Consistent with complement activation co-localization of synaptophysin and C1q was observed. (J,K) TGFb family gene expression in wild type and Abcd1−/− spinal cord at 2 months and 15 months of age (n=12) is shown. Data were expressed as mean±SEM, *P<0.05, **P<0.01.
Figure 3B:
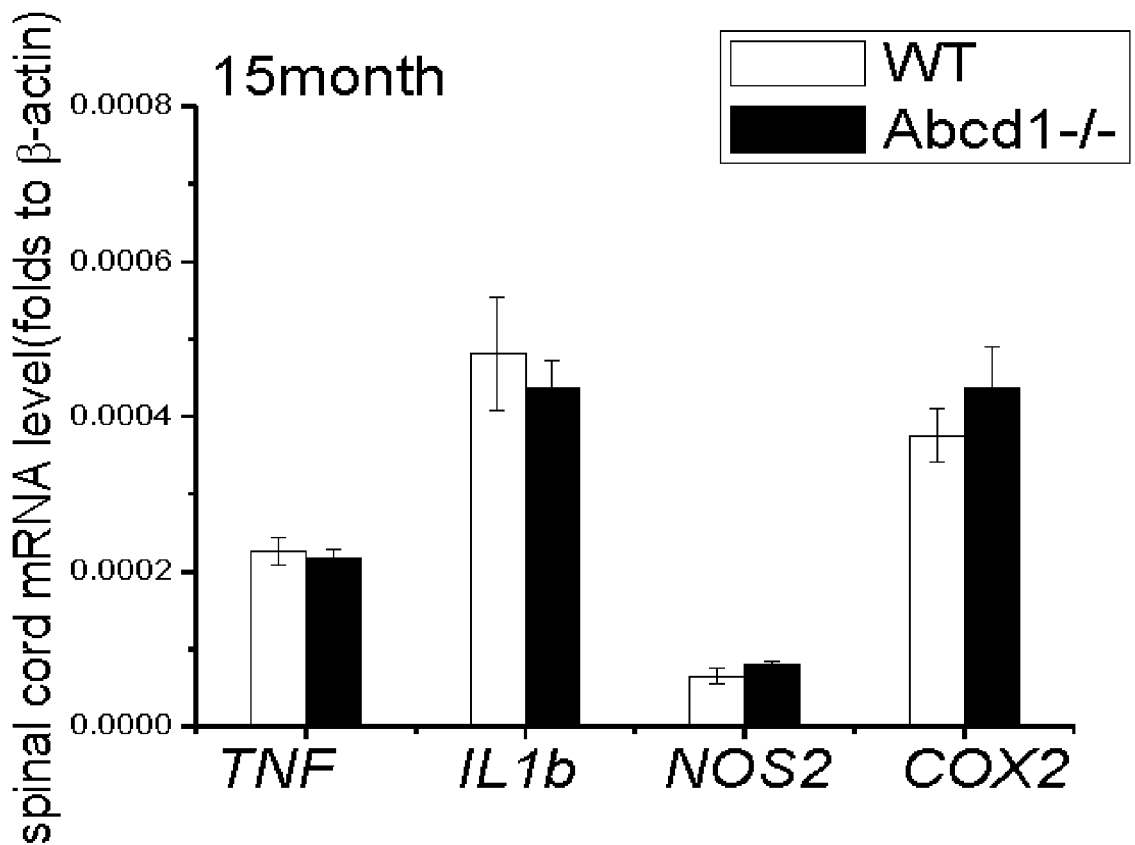
Figure 3C:
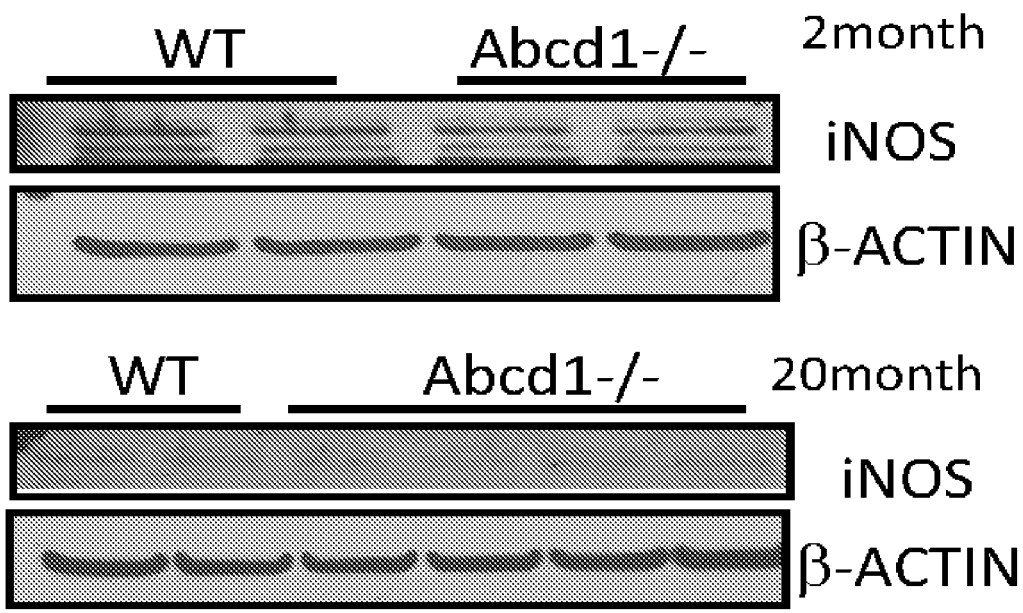

Example 2. Abcd1−/− Mouse Spinal Cord Displays a Lack of Proinflammatory Markers but Increase in Phagocytosis-Related Molecule Expression In order to determine whether inflammation is involved in AMN disease progression, measured several proinflammatory biomarkers that are usually upregulated during inflammation were measured. At both 2 and 15 months, no significant changes in expression of proinflammatory genes and proteins were detected in Abcd1−/− mouse spinal cord (FIGS. 3A, 3B, 3C).

Figure 3D:
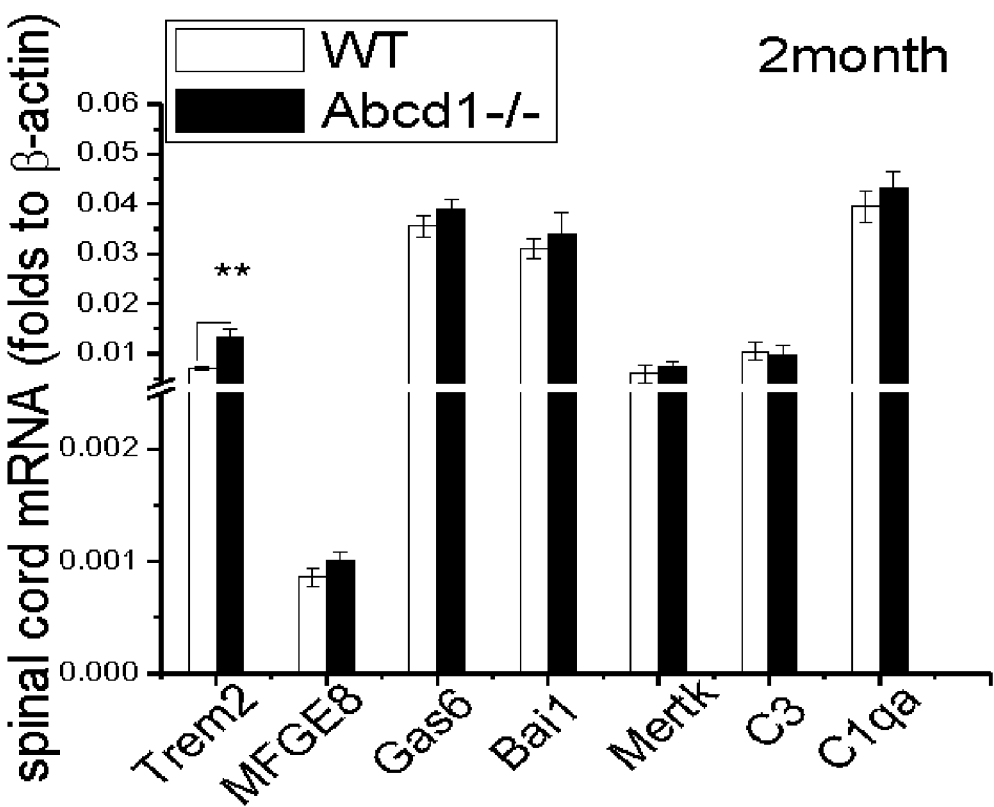
Figure 3E:
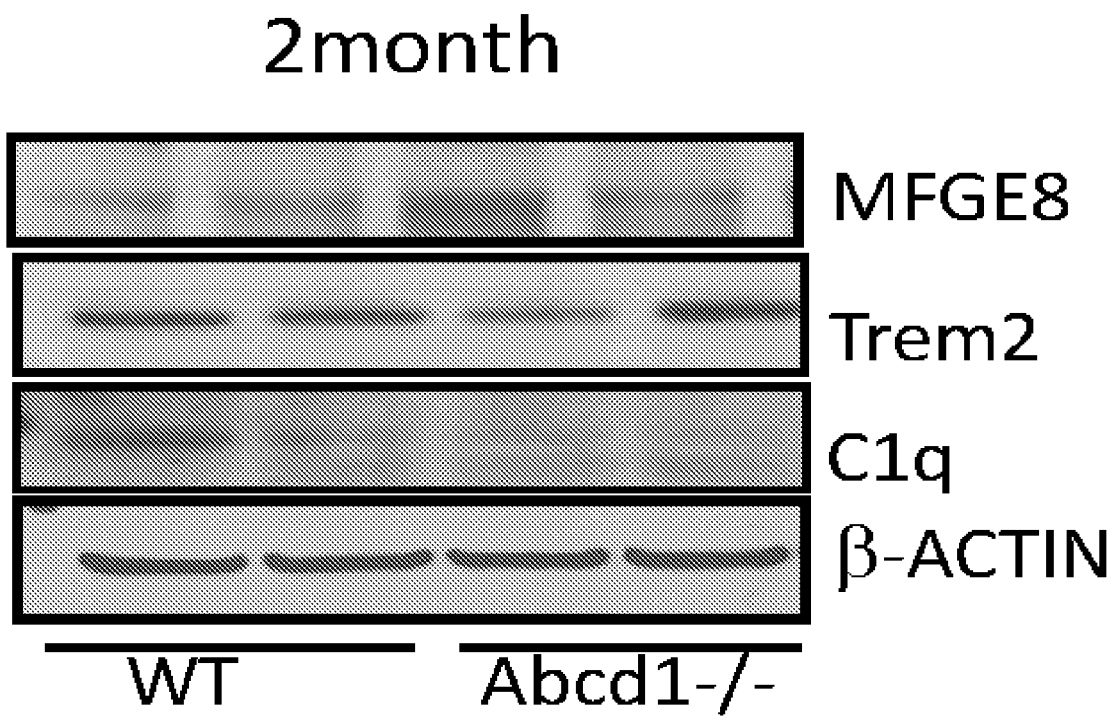
Figure 3F:
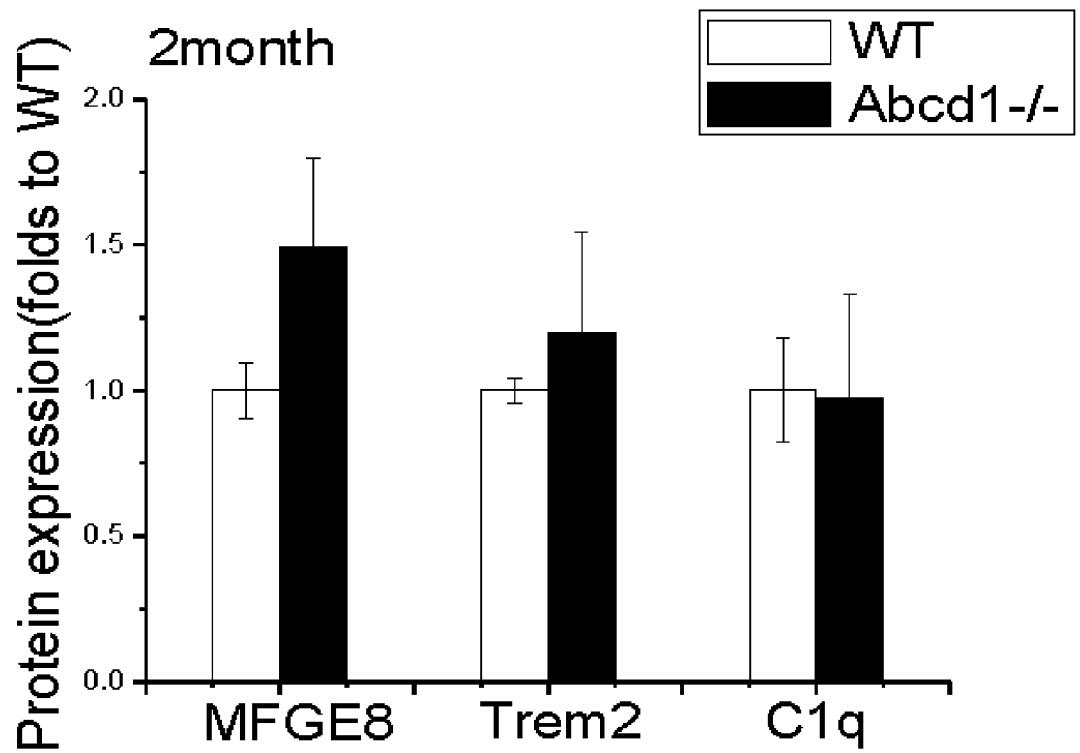
Figure 3G:
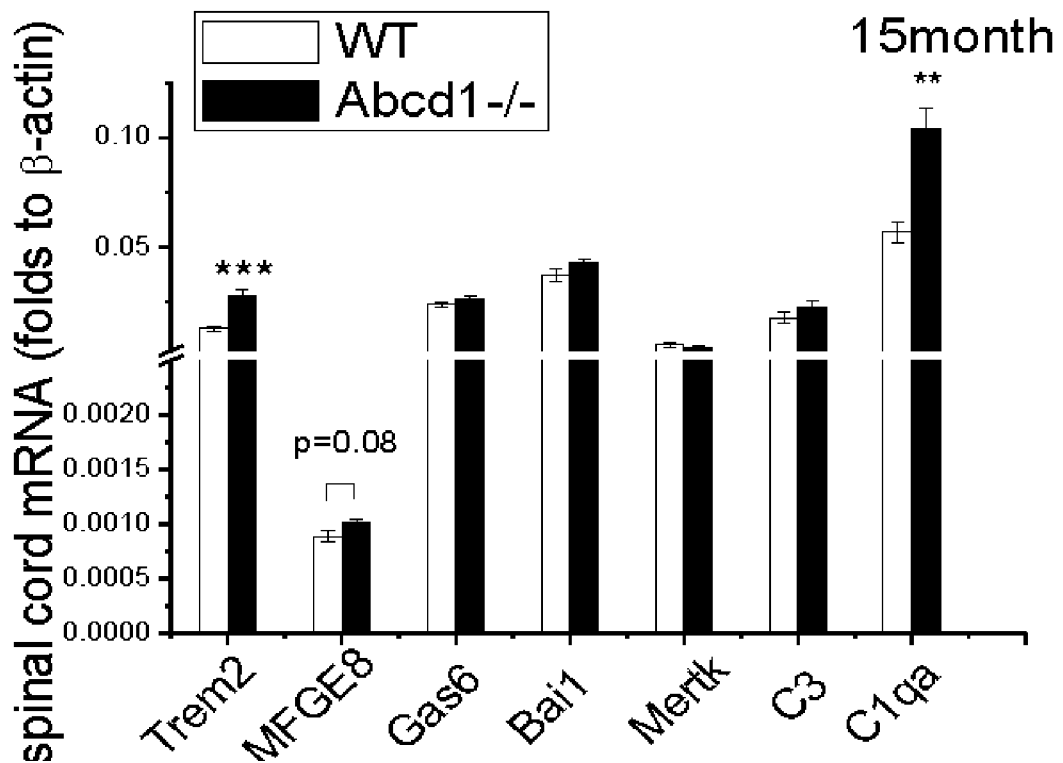
Figure 3H:
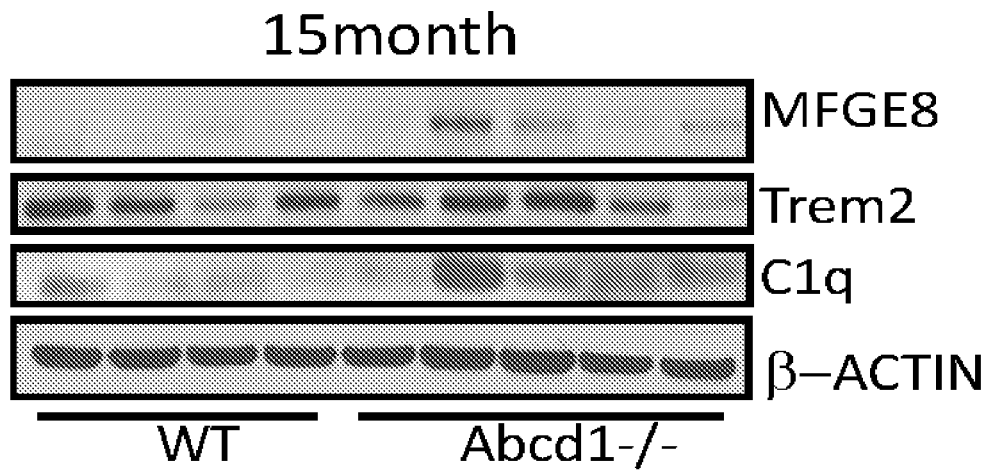
Figure 3I:
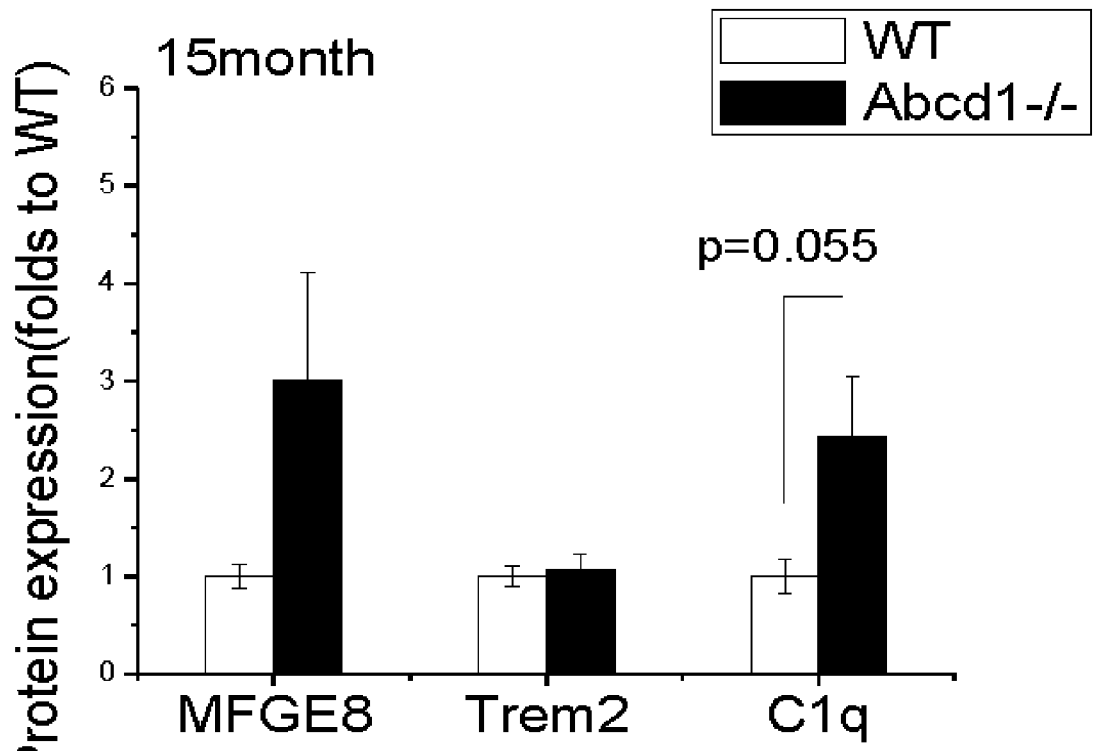
Figure 3J:
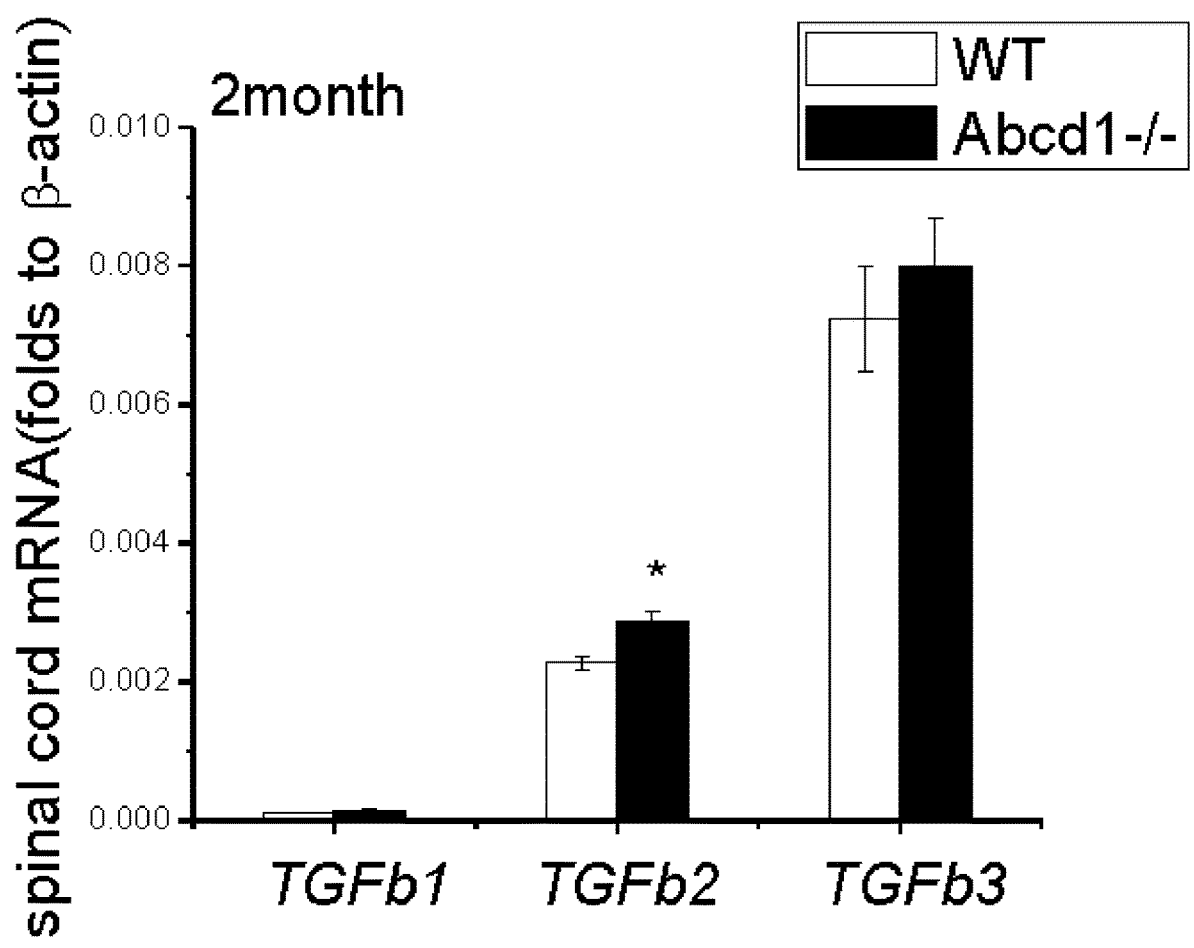
Figure 3K:
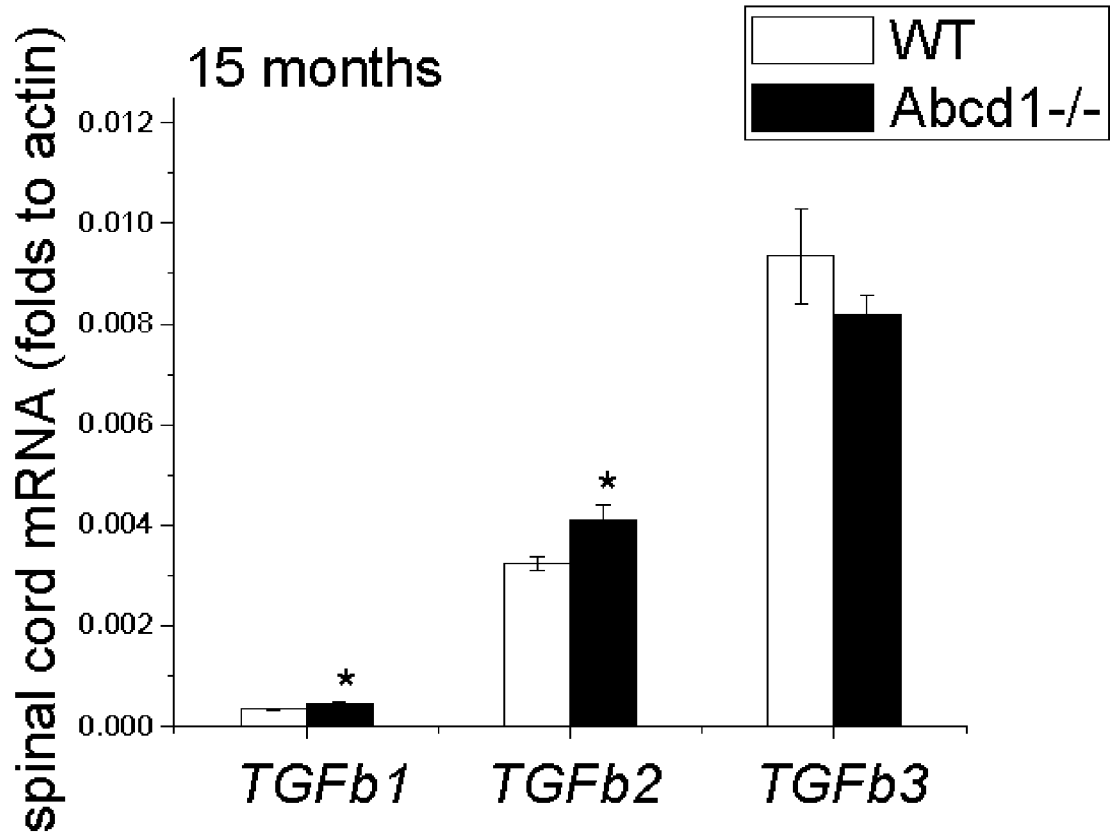

Next, the expression of several key receptors and signaling molecules for phagocytosis was determined. Surprisingly, there was a significant increase of Trem2 gene expression (as well as minor but not significant increases in C1qa, MFGE8, Gash and Bai1) in the spinal cord of young 2 month old Abcd1−/− mice (FIGS. 3D, 3E, 3F). By 15 months of age, a remarkable upregulation of Trem2, C1qa and MFGE8 mRNA was evident (FIG. 3G, $P<0.05$), coinciding with prominent C1q and MFGE8 protein upregulation (FIGS. 3H and 3I). Co-staining of synaptophysin and C1q at different ages showed frequent co-localization suggesting a role of C1q in synaptic pruning and axonal degeneration. Interestingly, the TGFb family of genes, especially TGFb2, that is known to regulate C1q and MFGE8, showed significant upregulation at both 2 and 15 months (FIGS. 3J and 3K).

Example 3. In Vitro, ABCD1 Deficient Microglia Lack an Inflammatory Profile but Increase Phagocytosis of Phosphatidylserine (PS) Exposing Neurons In order to learn whether microglial changes seen in vivo were primary or secondary to axon degeneration, microglia was isolated from postnatal mice and molecular changes in unstimulated conditions was assessed as well as after LPS challenge. Microglia cultures were prepared as previously described (Tamashiro et al., 2012). Briefly, mixed glial cultures (~95% astrocytes, ~5% microglia) were prepared from the brain tissue of 1-3 day old mice. The tissue was trypsinized with 0.05% trypsin, and the cells were resuspended in glia complete medium DMEM (Lonza) supplemented with 10% fetal bovine serum (FBS), 100 IU/ml penicillin, 100 µg/ml streptomycin and 2 mM L-Glutamine. After 10-14 days in culture, microglia were isolated from the mixed glial cultures by the shake-off procedure. Specifically, loosely attached microglia were obtained from an incubator shaker at 250 rpm for 2 h at 37° C., the cell-containing medium was centrifuged at 1100 rpm for 3 minutes to collect microglia for subsequent culture. N9 microglia cells were cultured in RPMI 1640 medium supplemented with 10% FBS.

Figure 4A:
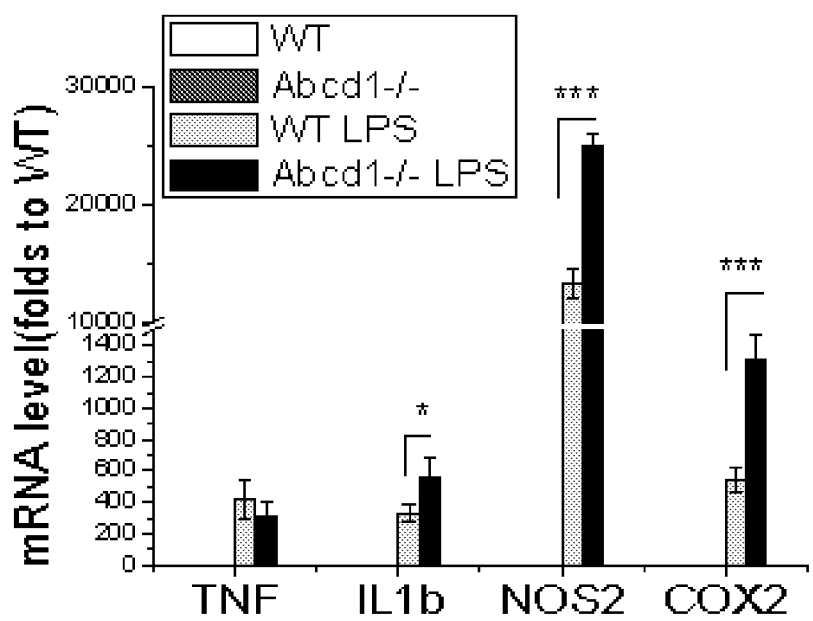
FIGS. 4A-4G depict Abcd1−/− microglia lacking an inflammatory profile but having an increased phagocytosis of phosphatidylserine (PS) exposing apoptotic neurons. (A) Proinflammatory genes including IL1b, TNF, NOS2 and Cox2 did not show distinct alterations between wild type and Abcd1−/− microglia at basal level, whereas LPS treatment for 6 h dramatically increased these gene expression in both wild type and Abcd1−/− microglia with more enhanced response from Abcd1−/−. (B) The general microglial marker IBA1 and CD11b showed some increased expression at base level. (C) Phagocytosis related genes including Trem2, MFGE8, Gash, and Bai1 were all upregulated in Abcd1−/− mouse microglia, but not C3 and C1qa, at both unstimulated and LPS challenged conditions with MFGE8 showing the most significant increase. LPS challenge decreased the phagocytosis related genes except for C3. (D) ELISA of microglia culture medium confirmed higher MFGE8 expression in Abcd1−/− microglia at both basal and LPS treated conditions. Imaging showed Abcd1−/− microglial phagocytosis of PS exposed SH-Sy5y neurons (CMTPX). (E) Quantification of red granules within IBA1 stained microglia showed a trend to increase phagocytosis of PS exposing SH-Sy5y neuron in Abcd1−/− microglia at both basal and LPS stimulated conditions. (F) Supplementation of MFGE8 dramatically increased microglial phagocytosis of PS exposing neurons. (G) MFGE8 antibody treatment reduced microglia phagocytosis of PS exposing neurons. Bar=50 μm. Data were expressed as mean±SEM, *P<0.05, P<0.01, *P<0.001.
Figure 4B:
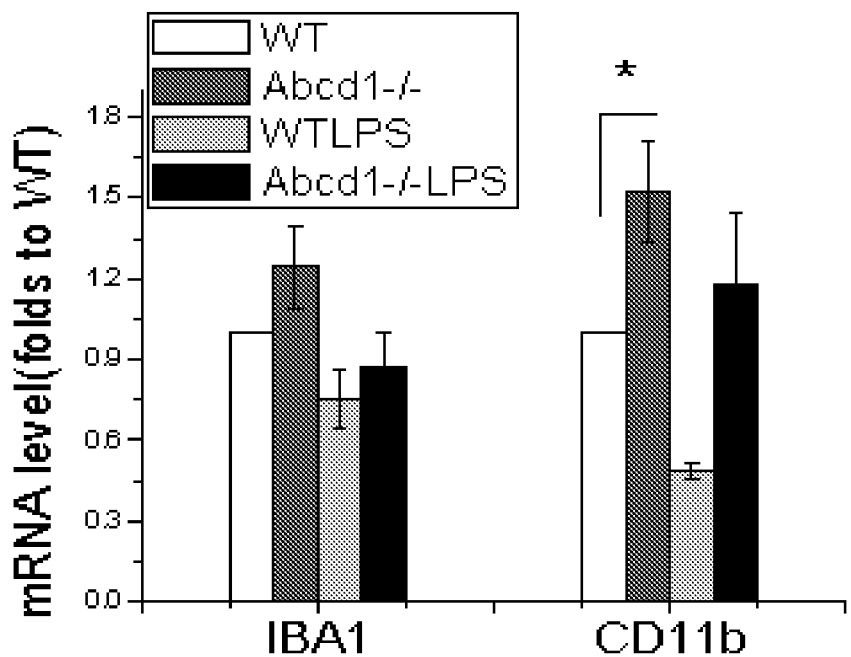

In a quiescent state, the expression of several major proinflammatory biomarkers including IL1β, TNF, NOS2, Cox2 were very low in Abcd1−/− mice. However, an LPS challenge (1 µg/ml) led to an upregulation in mRNA of IL1β, NOS2 and Cox2, suggesting microglia in Abcd1−/− mice are primed to respond to stimuli (FIG. 4A). Higher IBA1 and CD11b expression was detected in both quiescent and LPS challenge states (FIG. 4B).

Figure 4C:
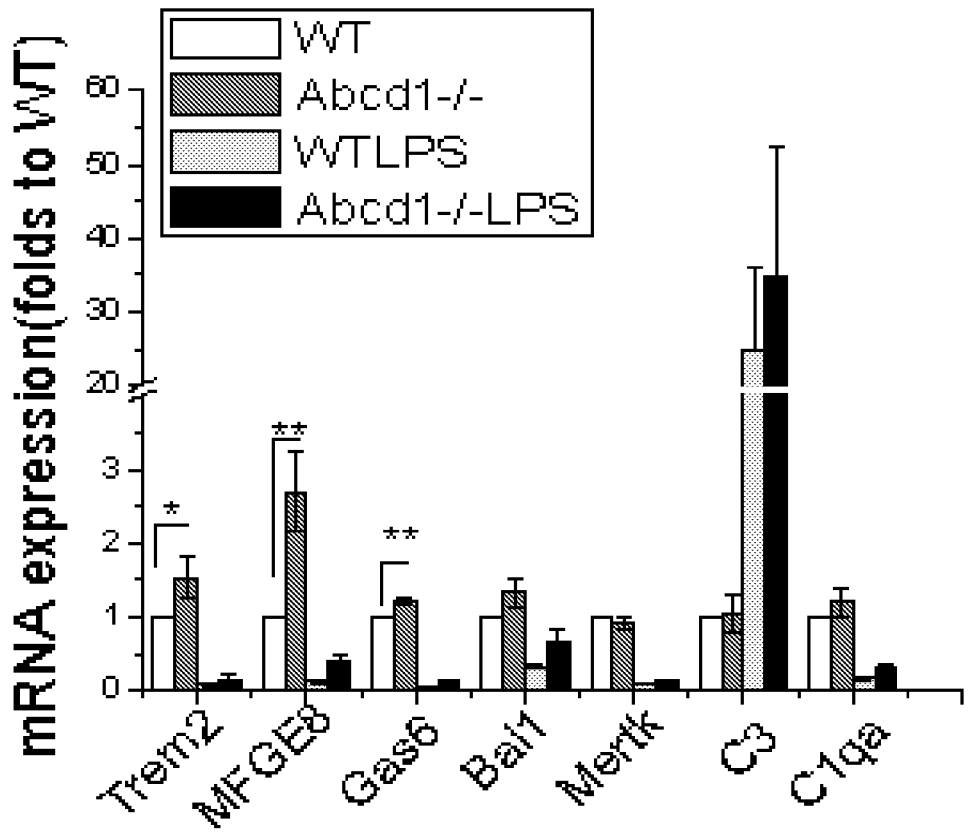

After observing an unexpected increase of phagocytosis-related biomarkers at the tissue level, whether gene expression of these markers would be altered in vitro was examined. Total RNA from cells or tissues were isolated using Qiagen RNeasy Mini Kit (Qiagen). First-strand cDNA synthesis used 100 ng random primer (Life Technologies), 1.0 total RNA, 10 mM dNTP, and 200 units of reverse transcriptase (Life Technologies) per 20 µL reactions. PCRs were performed in duplicates in a 25 µl final volume by using SYBR Green master mix from Applied Biosystems (Life Technologies). The data was analyzed by calculating the delta Ct value between the tested gene and an internal control. Indeed significantly higher levels of Bai1, Gash, MFGE8 and Trem2 were observed in Abcd1−/− microglia, with MFGE8 displaying a 3-fold increase (FIG. 4C, $P<0.05$).

Figure 4D:
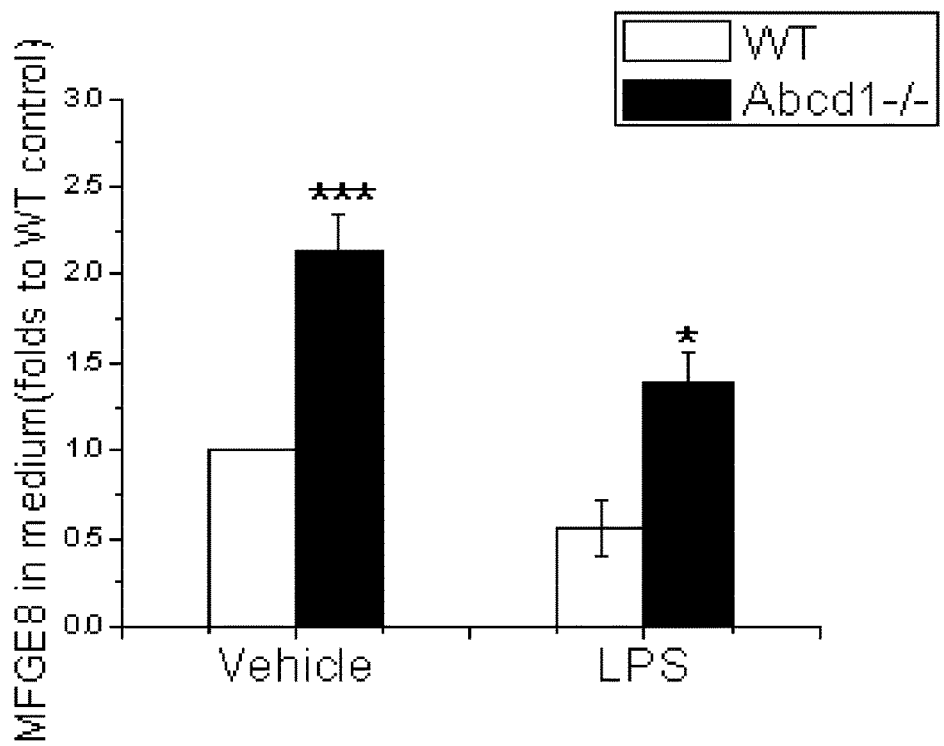

An ELISA assay detected 2-fold higher MFGE8 protein secretion into media by Abcd1−/− microglia (FIG. 4D, $P<0.05$; MFGE8 and TNFa level in culture medium and spinal cord homogenate were measured using MFGE8 and TNFa ELISA kit (R&D) according to manufacturer's instructions).

Figure 4E:
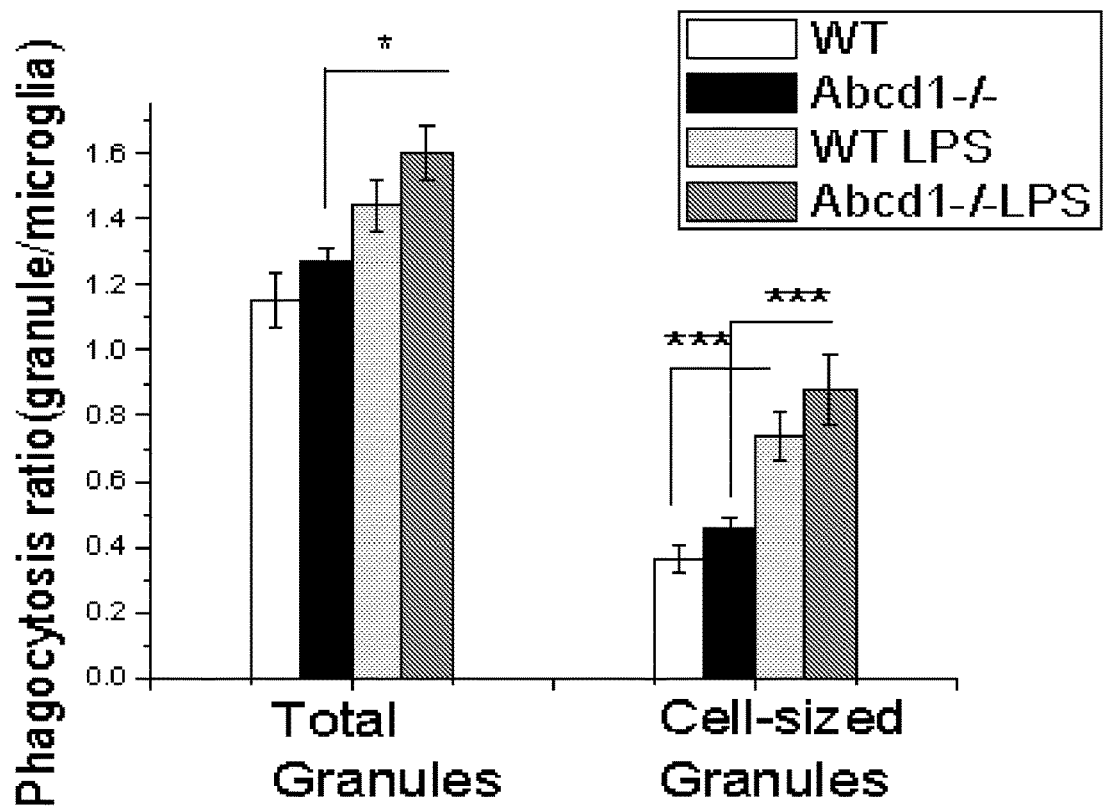

As a bridging protein, MFGE8 tightly binds to exposed phosphatidylserine on surface membranes of stressed neurons and opsonizes them for phagocytosis. Indeed, in co-culture, Abcd1−/− microglia increased phagocytosis of phosphatidylserine-exposing neurons in both unstimulated and LPS-challenged conditions (FIG. 4E). For the co-culture of microglia and neurons, isolated microglia were seeded on top of differentiated neurons and co-cultured for 4 days with or without supplementation of VLCFA. For VLCFA supplementation, hexacosanoic acid (FFA C26:0) and Lysophosphatidylcholine (LPC) C16:0 and C26:0 (Avanti polar lipid) were solubilized in 50 mg/ml Methyl-β-cyclodextrin to make 3 mM stock solution and then supplemented into culture medium to reach designated concentration with Methyl-β-cyclodextrin as vehicle control. After co-culture for 4 days, cells were fixed in PFA and immunostained with Tuj-1, which is a β-Tubulin family structural protein expressed in neurons and IBA1 that marks microglia. Tuj-1 immunofluoresece and degenerated axons were quantified in each group.

To validate the impact of MFGE8, primary microglia from Abcd1−/− mice were pretreated with either MFGE8 (50 ng/ml) or MFGE8 antibody for 12 hours and then phagocytosis was assessed by performing a microglial phagocytosis assay. Microglia were seeded in 8-well chamber (7×10⁴/well in complete medium) and cultured for 24 hours. SH-SY5Y cells were treated with 100 uM $H_2O_2$ for 12 hours to induce phosphatidylserine (PS) exposure on cell surface. Floating SH-Sy5Y cells were then collected by centrifuge at 1000 g for 3 minutes, resuspended in serum free medium and stained with 3 µM CMTPX (red)(Life Science Technologies)(1:1000 dilution) for 30 minutes. A portion of the floating cells was subjected to Annexin V-FITC staining to confirm the exposure of phosphatidylserine. The remnant was washed twice and seeded (same amount as microglia) on top of the microglial layer. After 4 hours co-culture, cells were washed with PBS and fixed with 4% paraformaldehyde (PFA) for 15 min at room temperature. Microglia were then stained with IBA1 antibody (Wako) overnight followed by Alexa Fluor-488 conjugated second antibody. For quantification, 5 random images were taken from each chamber well using a confocal microscope (Zeiss). The total number of phagocytosed particles as well as cell-sized particles was counted and divided by microglia cell number.

Figure 4F:
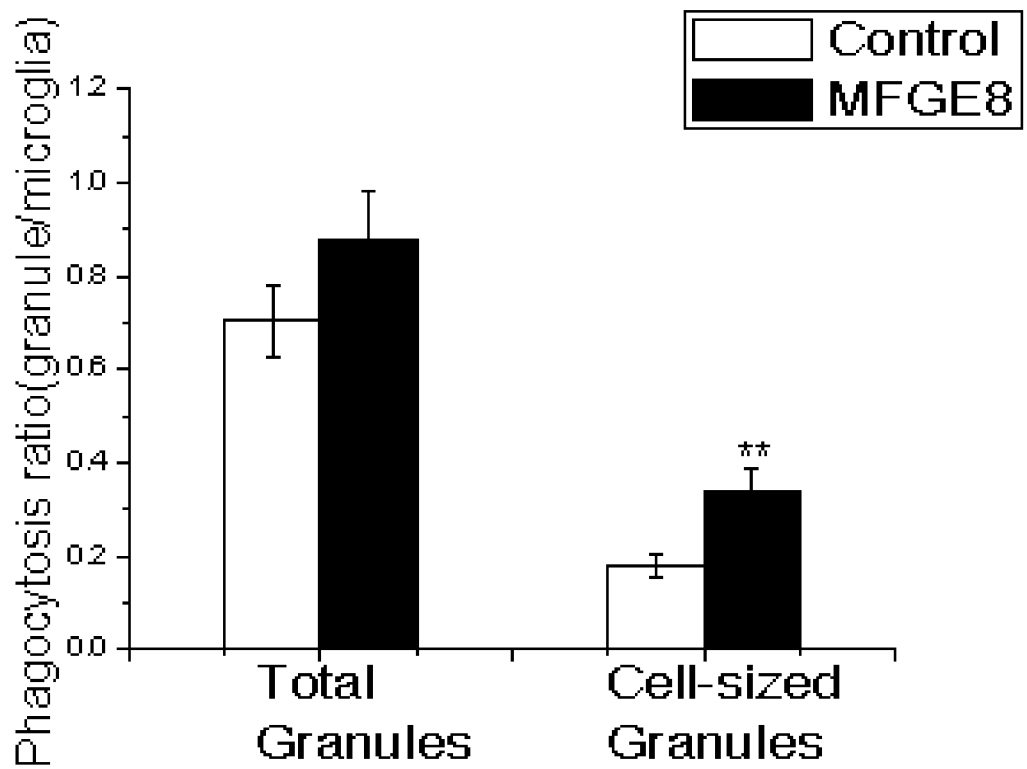
Figure 4G:
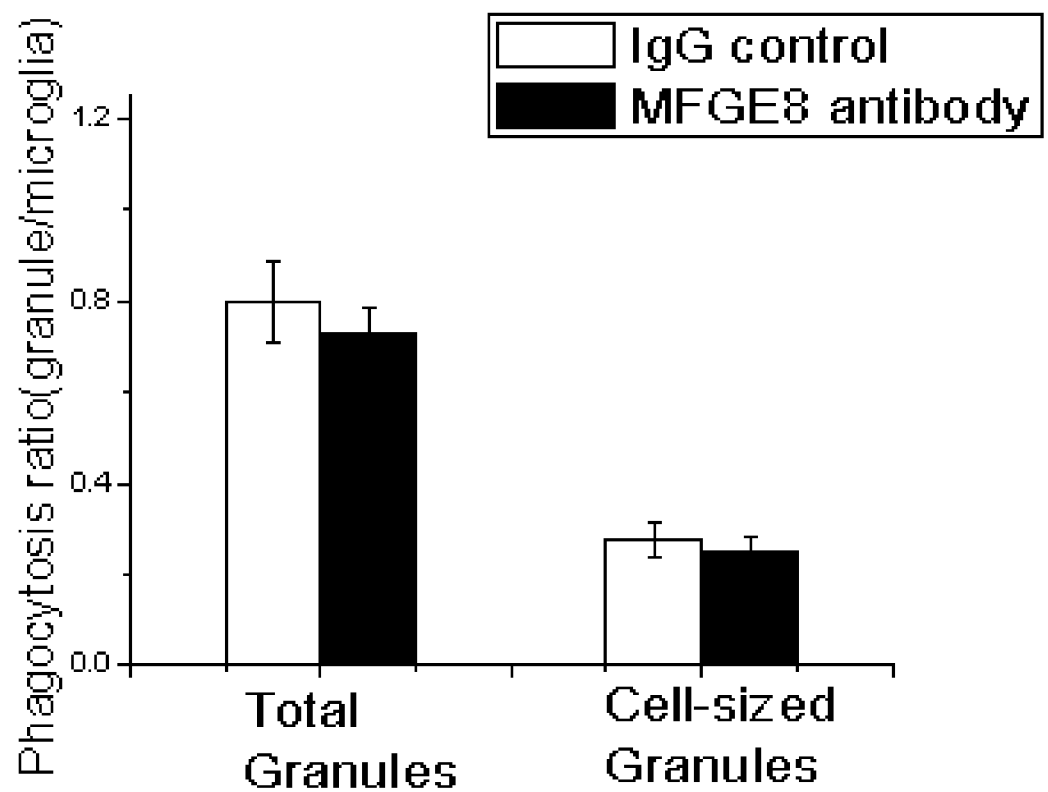

A significant increase in phagocytosis in MFGE8 treated microglia (FIG. 4F, P<0.05) was observed, whereas exposure to MFGE8 antibody reduced phagocytic capacity (FIG. 4G). These data suggest that genetic ablation of ABCD1 leads to increased secretion of MFGE8 by microglia and thereby contributes to phagocytosis of stressed neurons.

Example 4. Lysophosphatidylcholine (LPC) C26:0 Treatment Exposes Phosphatidylserine on the Neuronal Cell Surface The most significant biochemical change caused by ABCD1 mutations is increased VLCFA levels including free fatty acid and LPC (in particular C24:0 and C26:0) in plasma and tissues. In order to determine whether neurons exposed to high VLCFA levels have PS exposure on their surfaces, neurons differentiated from ReN cells were treated with both C26:0 free fatty acid (FFA C26:0) and LPC C26:0 and then determined the PS exposure by Annexin V-FITC binding. Immortalized hNPC cell line ReNcell VM (ReN) was used to differentiate into neurons according to a published protocol (Kim et al., 2015). Simply, ReN cells were grown in proliferation medium (DMEM/F12 (Gibco/Life Technologies) with 2 µg/ml heparin (stock, STEMCELL Technologies), 2% B27 (Life Technologies), 20 ng/ml EGF, 20 ng/ml bFGF and 1% of 100× penicillin/streptomycin (Gibco/Life Technologies) until confluency. For differentiation, $3 \times 10^4$ cells were seeded on matrigel-coated (1:100 dilution in DMEM/F12) 8 well chamber slides and grown in differentiation medium (DMEM/F12 (Gibco/Life Technologies) with 2 µg/ml heparin (stock, STEMCELL Technologies), 2% B27 (Life Technologies) and 1% of 100× penicillin/streptomycin (Gibco/Life Technologies) for 2-3 weeks prior to co-culture with microglia.

Figure 5:
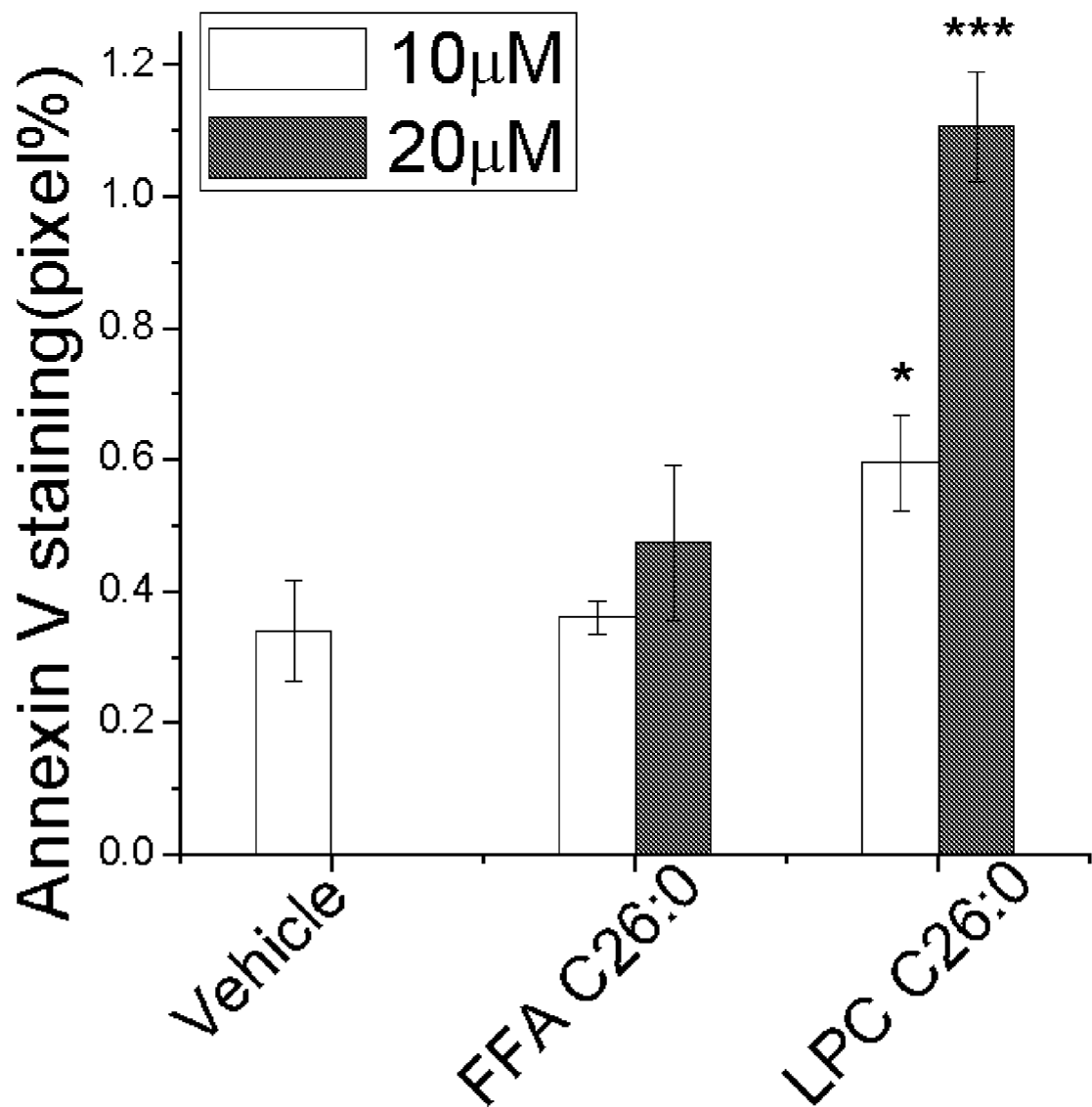
FIG. 5 depicts Lysophosphatidylcholine (LPC) C26:0 treatment induced phosphatidylserine (PS) exposure. Annexin V staining showed exposure of phosphatidylserine (PS) on the outer cell membrane of differentiated ReN (neuron cells) after 20 uM LPC C26:0 treatment. Tuj 1 and cleaved-caspase staining showed little late apoptosis by LPC C26:0 treatments. The graph shows quantification of Annexin V-FITC fluorescence using image J. Data were expressed as mean±SEM, *P<0.05, P<0.01, *P<0.001.

As displayed in FIG. 5, FFA C26:0 treatment for 3 days at either 10 µM or 20 µM did not induce significant PS exposure on cell surface. However, there was a remarkable dose dependent PS exposure after LPC C26:0 treatment at both 10 µM and 20 µM. Further staining with cleaved-caspase did not reveal a notable positive signal with either FFA C26:0 or LPC C26:0 treatment. In addition, the neuronal marker Tuj 1 did not show significant morphological changes, suggesting neurons were still alive after LPC C26:0 treatment despite PS exposure.

Example 5. LPC C26:0 Enhances MFGE8 Expression in Microglia

Figure 6A:
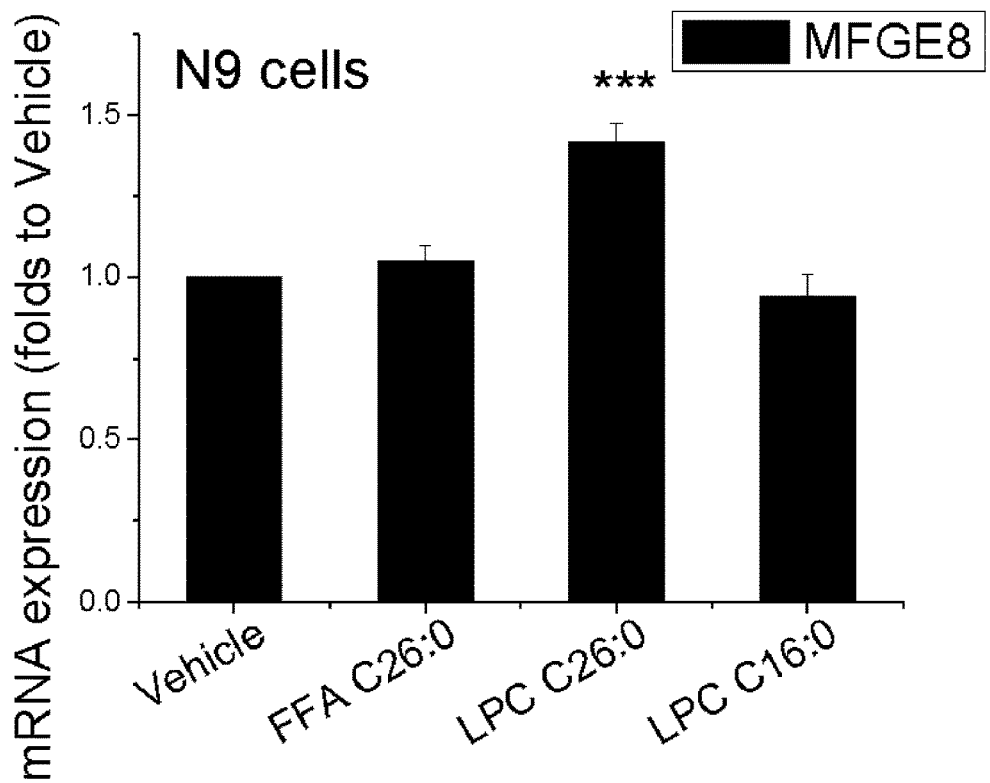
FIGS. 6A-C depict LPC C26:0 enhanced MFGE8 expression in Abcd1−/− microglia. (A) The effect of free fatty acid (FFA) C26:0 (30 uM) and LPC C26:0 (30 uM) and LPC C16:0 (30 uM) on MFGE8 gene expression in wild type N9 microglia is shown. (B) The effect of 15 uM LPC C26:0 treatment on MFGE8 gene expression in primary isolated microglia from wild type and Abcd1−/− mice is shown. MFGE8 expression is compared to untreated wild type primary microglia as Abcd1−/− microglia have higher levels of MFGE8 at baseline (see FIG. 4C). (C) The effect of 15 uM LPC C26:0 treatment on MFGE8 protein secretion in primary isolated microglia from wild type and Abcd1−/− mice is shown. Data were expressed as mean±SEM, *P<0.05, P<0.01, *P<0.001.
Figure 6B:
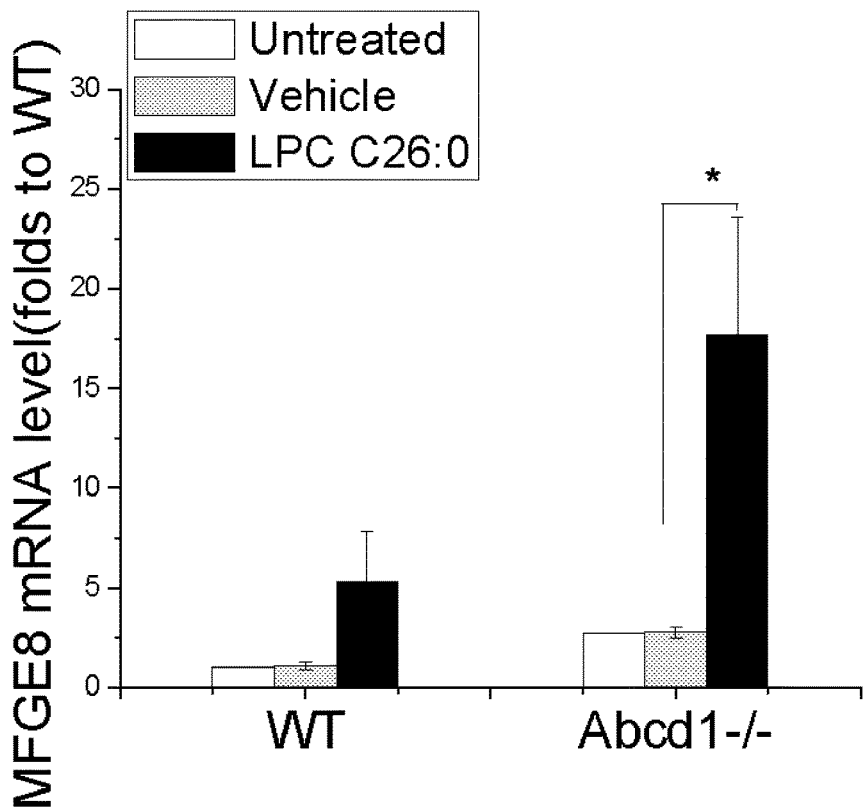
Figure 6C:
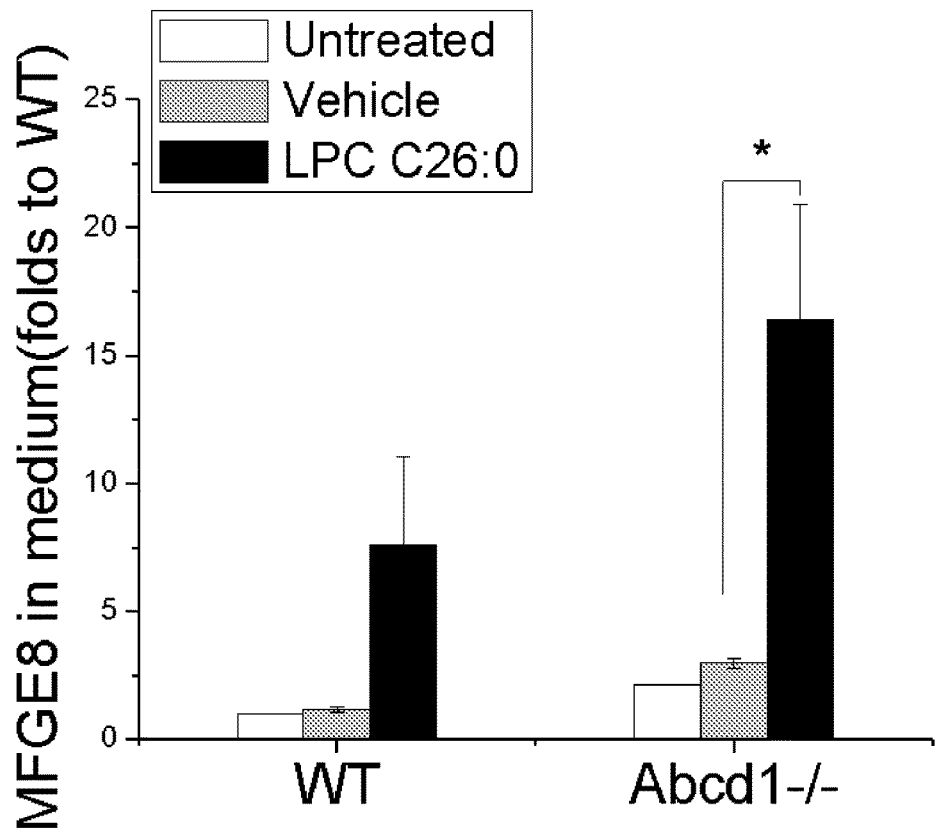

In order to examine whether VLCFA has any effect on MFGE8 expression, microglial cell lines (N9) were treated with 30 uM FFA C26:0, LPC C16:0 and LPC C26:0 separately for 3 days. As was shown in FIG. 6A, LPC C26:0 significantly increased MFGE8 mRNA expression while FFA C26:0 and LPC C16:0 did not have an effect. Finally, primary isolated microglia from both WT and Abcd1−/− mice were treated with 15 uM LPC C26:0 and significant increases of MFGE8 expression at both mRNA (FIG. 6B, P<0.05) and protein level (FIG. 6C, P<0.05) were observed.

Example 6. LPC C26:0 Mediates Damage to Neurons in the Presence of ABCD1 Deficient Microglia To assess whether Abcd1−/− microglia have a direct impact on neurite growth, microglia were isolated from wild type and Abcd1−/− mice and then co-cultured with differentiated neurons for 4 days. In this co-culture, no change in neurite density and morphology was observed, suggesting Abcd1−/− microglia alone have no direct impact on neurite growth in vitro (FIG. 7A). However, when 15 uM LPC C26:0 was supplied, it decreased Tuj 1 expression by 20%, implying damage to the neuron in the co-culture system (FIG. 7B), and treatment with MFGE8 antibody (MFGE8 Ab) in the co-culture system slightly alleviated the adverse impact (FIG. 7B). Higher magnification images show microglia phagocytosing neuron in the LPC C26:0 supplemented co-culture system, with degenerated axons frequently seen. Quantification data indicated increased axon degeneration after LPC C26:0 supplementation in the co-culture system while MFGE8 antibody treatment exhibits some protective effect on axon degeneration (FIG. 7C).

Example 7. Human AMN Spinal Cord Displays Microglia Activation and Increased Expression of Phagocytosis Related Markers and Synaptic Dysfunction To determine whether the observation in AMN mice were applicable to humans, spinal cord tissue from a pure AMN human patient encompassing the corticospinal tract and dorsal columns was examined. Luxol fast blue (LFB) staining shows reduced myelin staining in dorsal column of AMN spinal cord, demonstrating mild myelin loss commensurate with axonal loss. Dramatic increases in CD68 and IBA1 staining in AMN spinal cord were also observed compared to the control group, suggesting activation of microglia in the spinal cord of AMN. Next, the spinal cord from another 13 postmortem adult ALD tissues (FIGS. 8A-8D) was analyzed. Initial analysis was performed separately for patients who by history were thought to have cerebral ALD alone versus cerebral ALD plus AMN. As the spinal cord showed no significant differences and all male patients in adulthood manifest some degree of AMN, data were grouped and displayed as adult ALD only. As in mice, all human ALD spinal cord tissue displayed a dramatic increase in microglial activation in the spinal cord of AMN (FIGS. 8A-8D). Gene profiling showed significantly increased microglia activation markers (IBA1 and CD68) and phagocytosis markers (MFGE8 and C1qa) in the absence of a pro-inflammatory profile. Significant reduction in SYP gene expression indicated synaptic dysfunction in ALD spinal cord. Different from mice, some human ALD spinal cord showed perivascular macrophages with significant increases in Ccl2 and Ccr2 (FIG. 8A), indicating infiltration of monocytes.

REFERENCES

All patents, patent applications and publications mentioned in this specification are herein incorporated by reference to the same extent as if each independent patent and publication was specifically and individually indicated to be incorporated by reference.

1. Berger, J., Forss-Petter, S., and Eichler, F. S. (2014). Pathophysiology of X-linked adrenoleukodystrophy. Biochimie 98, 135-142.
2. Brown, G. C., and Neher, J. J. (2014). Microglial phagocytosis of live neurons. Nature reviews Neuroscience 15, 209-216.
3. Brown, G. C., and Vilalta, A. (2015). How microglia kill neurons. Brain research 1628, 288-297.

4. Butovsky, O., Siddiqui, S., Gabriely, G., Lanser, A. J., Dake, B., Murugaiyan, G., Doykan, C. E., Wu, P. M., Gali, R. R., Iyer, L. K., et al. (2012). Modulating inflammatory monocytes with a unique microRNA gene signature ameliorates murine ALS. The Journal of clinical investigation 122, 3063-3087.
5. Dumser, M., Bauer, J., Lassmann, H., Berger, J., and Forss-Petter, S. (2007). Lack of adrenoleukodystrophy protein enhances oligodendrocyte disturbance and microglia activation in mice with combined Abcd1/Mag deficiency. Acta neuropathologica 114, 573-586.
6. Eichler, F. S., Ren, J. Q., Cossoy, M., Rietsch, A. M., Nagpal, S., Moser, A. B., Frosch, M. P., and Ransohoff, R. M. (2008). Is microglial apoptosis an early pathogenic change in cerebral X-linked adrenoleukodystrophy? Annals of neurology 63, 729-742.
7. Fricker, M., Neher, J. J., Zhao, J. W., Thery, C., Tolkovsky, A. M., and Brown, G. C. (2012). MFG-E8 mediates primary phagocytosis of viable neurons during neuroinflammation. The Journal of neuroscience: the official journal of the Society for Neuroscience 32, 2657-2666.
8. Gong, Y., Mu, D., Prabhakar, S., Moser, A., Musolino, P., Ren, J., Breakefield, X. O., Maguire, C. A., and Eichler, F. S. (2015). Adenoassociated virus serotype 9-mediated gene therapy for x-linked adrenoleukodystrophy. Molecular therapy: the journal of the American Society of Gene Therapy 23, 824-834.
9. Hein, S., Schonfeld, P., Kahlert, S., and Reiser, G. (2008). Toxic effects of X-linked adrenoleukodystrophy-associated, very long chain fatty acids on glial cells and neurons from rat hippocampus in culture. Human molecular genetics 17, 1750-1761.
10. Ho, J. K., Moser, H., Kishimoto, Y., and Hamilton, J. A. (1995). Interactions of a very long chain fatty acid with model membranes and serum albumin. Implications for the pathogenesis of adrenoleukodystrophy. The Journal of clinical investigation 96, 1455-1463.
11. Hong, S., Beja-Glasser, V. F., Nfonoyim, B. M., Frouin, A., Li, S., Ramakrishnan, S., Merry, K. M., Shi, Q., Rosenthal, A., Barres, B. A., et al. (2016). Complement and microglia mediate early synapse loss in Alzheimer mouse models. Science 352, 712-716.
12. Hubbard, W. C., Moser, A. B., Liu, A. C., Jones, R. O., Steinberg, S. J., Lorey, F., Panny, S. R., Vogt, R. F., Jr., Macaya, D., Turgeon, C. T., et al. (2009). Newborn screening for X-linked adrenoleukodystrophy (X-ALD): validation of a combined liquid chromatography-tandem mass spectrometric (LC-MS/MS) method. Molecular genetics and metabolism 97, 212-220.
13. Igarashi, M., Schaumburg, H. H., Powers, J., Kishimoto, Y., Kolodny, E., and Suzuki, K. (1976). Fatty acid abnormality in adrenoleukodystrophy. Journal of neurochemistry 26, 851-860.
14. Kim, Y. H., Choi, S. H., D'Avanzo, C., Hebisch, M., Sliwinski, C., Bylykbashi, E., Washicosky, K. J., Klee, J. B., Brustle, O., Tanzi, R. E., et al. (2015). A 3D human neural cell culture system for modeling Alzheimer's disease. Nature protocols 10, 985-1006.
15. Kinsner, A., Pilotto, V., Deininger, S., Brown, G. C., Coecke, S., Hartung, T., and Bal-Price, A. (2005). Inflammatory neurodegeneration induced by lipoteichoic acid from *Staphylococcus aureus* is mediated by glia activation, nitrosative and oxidative stress, and caspase activation. Journal of neurochemistry 95, 1132-1143.
16. Lui, H., Zhang, J., Makinson, S. R., Cahill, M. K., Kelley, K. W., Huang, H. Y., Shang, Y., Oldham, M. C., Martens, L. H., Gao, F., et al. (2016). Progranulin Deficiency Promotes Circuit-Specific Synaptic Pruning by Microglia via Complement Activation. Cell 165, 921-935.
17. Mahmood, A., Raymond, G. V., Dubey, P., Peters, C., and Moser, H. W. (2007). Survival analysis of haematopoietic cell transplantation for childhood cerebral X-linked adrenoleukodystrophy: a comparison study. The Lancet Neurology 6, 687-692.
18. Moser, A. B., Kreiter, N., Bezman, L., Lu, S., Raymond, G. V., Naidu, S., and Moser, H. W. (1999). Plasma very long chain fatty acids in 3,000 peroxisome disease patients and 29,000 controls. Annals of neurology 45, 100-110.
19. Mosser, J., Douar, A. M., Sarde, C. O., Kioschis, P., Feil, R., Moser, H., Poustka, A. M., Mandel, J. L., and Aubourg, P. (1993). Putative X-linked adrenoleukodystrophy gene shares unexpected homology with ABC transporters. Nature 361, 726-730.
20. Mosser, J., Lutz, Y., Stoeckel, M. E., Sarde, C. O., Kretz, C., Douar, A. M., Lopez, J., Aubourg, P., and Mandel, J. L. (1994). The gene responsible for adrenoleukodystrophy encodes a peroxisomal membrane protein. Human molecular genetics 3, 265-271.
21. Neher, J. J., Emmrich, J. V., Fricker, M., Mander, P. K., Thery, C., and Brown, G. C. (2013). Phagocytosis executes delayed neuronal death after focal brain ischemia. Proceedings of the National Academy of Sciences of the United States of America 110, E4098-4107.
22. Neher, J. J., Neniskyte, U., Zhao, J. W., Bal-Price, A., Tolkovsky, A. M., and Brown, G. C. (2011). Inhibition of microglial phagocytosis is sufficient to prevent inflammatory neuronal death. Journal of immunology 186, 4973-4983.
23. Neniskyte, U., and Brown, G. C. (2013). Lactadherin/MFG-E8 is essential for microglia-mediated neuronal loss and phagoptosis induced by amyloid beta. Journal of neurochemistry 126, 312-317.
24. Powers, J. M. (1985). Adreno-leukodystrophy (adreno-testiculo-leukomyelo-neuropathic-complex). Clinical neuropathology 4, 181-199.
25. Powers, J. M., DeCiero, D. P., Ito, M., Moser, A. B., and Moser, H. W. (2000). Adrenomyeloneuropathy: a neuropathologic review featuring its noninflammatory myelopathy. Journal of neuropathology and experimental neurology 59, 89-102.
26. Pujol, A., Ferrer, I., Camps, C., Metzger, E., Hindelang, C., Callizot, N., Ruiz, M., Pampols, T., Giros, M., and Mandel, J. L. (2004). Functional overlap between ABCD1 (ALD) and ABCD2 (ALDR) transporters: a therapeutic target for X-adrenoleukodystrophy. Human molecular genetics 13, 2997-3006.
27. Pujol, A., Hindelang, C., Callizot, N., Bartsch, U., Schachner, M., and Mandel, J. L. (2002). Late onset neurological phenotype of the X-ALD gene inactivation in mice: a mouse model for adrenomyeloneuropathy. Human molecular genetics 11, 499-505.
28. Ran, F. A., Hsu, P. D., Lin, C. Y., Gootenberg, J. S., Konermann, S., Trevino, A. E., Scott, D. A., Inoue, A., Matoba, S., Zhang, Y., et al. (2013a). Double nicking by RNA-guided CRISPR Cas9 for enhanced genome editing specificity. Cell 154, 1380-1389.
29. Ran, F. A., Hsu, P. D., Wright, J., Agarwala, V., Scott, D. A., and Zhang, F. (2013b). Genome engineering using the CRISPR-Cas9 system. Nature protocols 8, 2281-2308.
30. Ransohoff, R. M., and El Khoury, J. (2015). Microglia in Health and Disease. Cold Spring Harbor perspectives in biology.

31. Schafer, D. P., Lehrman, E. K., Kautzman, A. G., Koyama, R., Mardinly, A. R., Yamasaki, R., Ransohoff, R. M., Greenberg, M. E., Barres, B. A., and Stevens, B. (2012). Microglia sculpt postnatal neural circuits in an activity and complement-dependent manner. Neuron 74, 691-705.

32. Schaumburg, H. H., Powers, J. M., Raine, C. S., Spencer, P. S., Griffin, J. W., Prineas, J. W., and Boehme, D. M. (1977). Adrenomyeloneuropathy: a probable variant of adrenoleukodystrophy. II. General pathologic, neuropathologic, and biochemical aspects. Neurology 27, 1114-1119.

33. Stephan, A. H., Madison, D. V., Mateos, J. M., Fraser, D. A., Lovelett, E. A., Coutellier, L., Kim, L., Tsai, H. H., Huang, E. J., Rowitch, D. H., et al. (2013). A dramatic increase of C1q protein in the CNS during normal aging. The Journal of neuroscience: the official journal of the Society for Neuroscience 33, 13460-13474.

34. Suzuki, J., Denning, D. P., Imanishi, E., Horvitz, H. R., and Nagata, S. (2013a). Xk-related protein 8 and CED-8 promote phosphatidylserine exposure in apoptotic cells. Science 341, 403-406.

35. Suzuki, J., Fujii, T., Imao, T., Ishihara, K., Kuba, H., and Nagata, S. (2013b). Calcium-dependent phospholipid scramblase activity of TMEM16 protein family members. The Journal of biological chemistry 288, 13305-13316.

36. Tamashiro, T. T., Dalgard, C. L., and Byrnes, K. R. (2012). Primary microglia isolation from mixed glial cell cultures of neonatal rat brain tissue. Journal of visualized experiments: JoVE, e3814.

37. Tyurina, Y. Y., Basova, L. V., Konduru, N. V., Tyurin, V. A., Potapovich, A. I., Cai, P., Bayir, H., Stoyanovsky, D., Pitt, B. R., Shvedova, A. A., et al. (2007). Nitrosative stress inhibits the aminophospholipid translocase resulting in phosphatidylserine externalization and macrophage engulfment: implications for the resolution of inflammation. The Journal of biological chemistry 282, 8498-8509.

38. van Geel, B. M., Koelman, J. H., Barth, P. G., and Ongerboer de Visser, B. W. (1996). Peripheral nerve abnormalities in adrenomyeloneuropathy: a clinical and electrodiagnostic study. Neurology 46, 112-118.

39. van Geel, B. M., Poll—The, B. T., Verrips, A., Boelens, J. J., Kemp, S., and Engelen, M. (2015). Hematopoietic cell transplantation does not prevent myelopathy in X-linked adrenoleukodystrophy: a retrospective study. Journal of inherited metabolic disease 38, 359-361.

40. Walport, M. J. (2001). Complement. First of two parts. N Engl J Med 344, 1058-1066.

41. Whitcomb, R. W., Linehan, W. M., and Knazek, R. A. (1988). Effects of long-chain, saturated fatty acids on membrane microviscosity and adrenocorticotropin responsiveness of human adrenocortical cells in vitro. The Journal of clinical investigation 81, 185-188.

The invention claimed is:

1. A method, comprising:
providing a biological sample from a spine of a human male subject diagnosed with X-linked adrenoleukodystrophy (X-ALD), and
detecting a level of milk fat globule-EGF factor 8 (MFGE8), complement C1q A chain (C1qa), triggering receptor expressed on myeloid cells 2 (Trem2), or growth arrest specific 6 (Gas6), in the sample.

2. The method of claim 1, wherein the biological sample is a biopsy of spinal tissue or spinal fluid.

3. The method of claim 1, comprising detecting a level of two or more of MFGE8, C1qa, Trem2, and Gas6.

4. The method of claim 1, comprising detecting a level of three or more of MFGE8, C1qa, Trem2, and Gas6.

5. The method of claim 1, comprising detecting a level of all four of MFGE8, C1qa, Trem2, and Gas6.

6. The method of claim 1, further comprising detecting one or both of tumor necrosis factor (TNF) alpha and interleukin 1 beta.

7. The method of claim 3, further comprising detecting one or both of tumor necrosis factor (TNF) alpha and interleukin 1 beta.

8. The method of claim 4, further comprising detecting one or both of tumor necrosis factor (TNF) alpha and interleukin 1 beta.

9. The method of claim 5, further comprising detecting one or both of tumor necrosis factor (TNF) alpha and interleukin 1 beta.

* * * * *